(12) United States Patent
Bikson et al.

(10) Patent No.: US 9,339,642 B1
(45) Date of Patent: May 17, 2016

(54) SYSTEM AND METHOD FOR CONDUCTING MULTI-ELECTRODE ELECTRICAL STIMULATION

(71) Applicant: Soterix Medical, Inc., New York, NY (US)

(72) Inventors: Marom Bikson, Brooklyn, NY (US); Lucas Cristobal Parra, Brooklyn, NY (US); Abhishek Datta, New York, NY (US); Niranjan Khadka, Jackson Heights, NY (US); Shiraz Azar Macuff, Hollis, NY (US)

(73) Assignee: Soterix Medical, Inc., New York, NY (US)

( * ) Notice: Subject to any disclaimer, the term of this patent is extended or adjusted under 35 U.S.C. 154(b) by 110 days.

(21) Appl. No.: 14/209,674

(22) Filed: Mar. 13, 2014

Related U.S. Application Data

(60) Provisional application No. 61/779,728, filed on Mar. 13, 2013.

(51) Int. Cl.
*A61N 1/00* (2006.01)
*A61N 1/04* (2006.01)
*A61N 1/36* (2006.01)

(52) U.S. Cl.
CPC .......... *A61N 1/0476* (2013.01); *A61N 1/36025* (2013.01)

(58) Field of Classification Search
CPC .................................................. A61N 1/0476
USPC ........................................................... 607/45
See application file for complete search history.

*Primary Examiner* — Nicole F Lavert
*Assistant Examiner* — Nadia A Mahmood
(74) *Attorney, Agent, or Firm* — Mintz Levin Cohn Ferris Glovsky and Popeo, P.C.

(57) ABSTRACT

In some embodiments of the present disclosure, systems and methods for effecting a physiological effect are provided. In some embodiments, a system is provided which comprises a plurality of current sources, where each current source having a positive output and a negative output and each being configured to provide a first current. The system may also include a plurality of stimulating electrodes electrically connected with the plurality of current sources such that at least a pair of the stimulating electrodes share at least one output of at least one of the plurality of current sources. The stimulating electrodes may be configured to provide electrical energy to tissue of a patient at the first current. The system may further include at least one sentinel electrode, and a first voltage monitor configured to monitor a first voltage across the at least one sentinel electrode and at least one of the plurality of stimulating electrodes.

30 Claims, 44 Drawing Sheets

SYSTEM AND METHOD FOR CONDUCTING MULTI-ELECTRODE ELECTRICAL STIMULATION

RELATED APPLICATIONS

This application claims priority to U.S. provisional patent application No. 61/779,728, filed Mar. 13, 2013, the entire disclosure of which is herein incorporated by reference.

FIELD OF THE DISCLOSURE

This disclosure relates to a system and method for conducting multi-electrode electrical stimulation for the purpose of producing changes in brain function while allowing for monitoring of electrode integrity or electrode-skin contact integrity during set-up or stimulation or post-stimulation, or system setup including electrode position and system performance.

BACKGROUND OF THE DISCLOSURE

Electrotherapy is therapy where electricity is applied to the body for medical purposes. One application of electrotherapy is where electrical stimulation is applied to the nervous system to improve neurological or psychiatric conditions. When electrical stimulation is applied though electrodes on the surface of the body, for example the scalp, it is non-invasive. In some systems, a minimum of two electrodes are required, but some systems utilize more electrodes to enhance targeting of brain regions. The waveform of stimulation describes the temporal pattern applied to the electrodes. The waveform of stimulation as applied to two or more electrodes determines the therapeutic actions.

SUMMARY OF SOME OF THE EMBODIMENTS

It is an object of some of the embodiments, to provide a system and method for conducting multi-channel electrical stimulation while monitoring the electrode quality such as, but not limited to, changes as might result from passage of current.

In some embodiments, an "Electrode Interface Impedance Tomography system" is provided, which may be referred to as the first general embodiment, which may comprise three or more electrodes, each of which may be non-invasive electrodes. Each electrode may be connected to one, or more energy sources. Electrodes connected to energy sources may be considered stimulating electrodes, according to some embodiments. In some embodiments, electrodes may also be connected to a second electrical energy source or to an electrical monitor, and referred to as sentinel electrodes. In some embodiments, sentinel electrodes may be connected to the second electrical energy source and may also be connected to the electrical monitor. In some embodiments, sentinel electrodes may be connected only to the electrical monitor.

The first electrical energy source may be current controlled and may be configured to produce electrical signals to produce electrical stimulation, neuromodulation, and/or therapeutic action. As such, the electrical signal is configured with sufficient intensity and waveform to effect a physiological change. For non-invasive direct current stimulation embodiments, the current may be between about 1 mA and about 2 mA of current, which may be applied for several minutes. As previously noted, in some embodiments, the electrical energy source may be connected to stimulating electrodes, and may be configured to control the amount of current delivered to each electrode to be controlled independently. One of skill in the art would understand that the first electrical energy source may be assembled from several independent components containing voltage of current sources. The function of these multiple components may be integrated through a microcontroller such that they work together in the first electrical energy sources (in such embodiments, not all components or all electrodes need to be energized or connected at any given time).

The second electrical energy source may be configured to produce electrical signals to facilitate monitoring of a parameter relevant to electrical stimulation of the actions of electrical stimulation, such as, for example, at least one of the quality and impedance of the electrodes. Thus, in some embodiments, the second electrical energy source may be distinct from the first source in that the electric current produced by the second energy source may not be primarily intended to produce neurophysiologic changes. This primary function does not exclude the possibility that such neurophysiologic changes may occur. It will be understood that the second electrical energy source does not need to be physically separate from the first electrical energy source. For example, a single current source may simultaneously provide two wave-forms, such as a sinusoid and DC source, where the sinusoid represent the second electrical energy source and the DC represent the first electrical energy source. Typically, the second electrical energy source is configured to minimize neurophysiologic response, for example, by decreasing the amplitude of voltage or current generated (e.g., 10 times less than the first energy source). In some embodiments, the waveform of the second electrical energy source may be altered to minimize physiologic consequences, for example, using high frequency sinusoid or short pulses. The second electrical energy sources may be composed of multiple individual elements, such as current controlled sources. In one embodiment, the output of the second electrical energy source may be controlled along three aspects: 1) the second electrical source may provide a signal that indicates the impedance of at least one of the electrodes that is generally indicative of the impedance of the electrode at zero HZ, or at is generally indicative of the impedance at a primary frequency of the first electrical energy source. For example, if the first electrical energy source provides DC current of low-intensity, the second electrical energy source can be configured to integrate the electrode with a signal consistent with the impedance associated with a DC current of low-intensity. In such a case, a very high frequency greater than 1000 Hz may not be effective. 2) the second electrical source may be configured to provide a signal that allows isolation of the impedance associated with an individual pair of electrodes and/or an individual electrode. For example, the second electrical source may provide to one or more electrodes, or each pair or electrodes, a unique frequency of sinusoidal current, or a pulse with a unique phase. In some embodiments, the signal from the second electrical source may be multiplexed using either time or frequency. While the second electrical source may differ from the first electrical source in several aspects (e.g., not primarily intended to activate a physiologic process), the second source should relate to the first electrical source in the nature of impedance scanning. Moreover, in some embodiments, while the first electrical source is configured to lack modulation for electrode separation, while the second source is. In some embodiments, a plurality of the electrodes connected to the first electrical source may be used by the second electrical source, but in some cases, additional electrodes may be used only by the second electrical source as "sentinel" electrodes of the first type.

In some embodiments, electrical ports are provided which may be each connected to the output of one or more energy sources. The electrical ports, in some embodiments, are configured to provide a means to connect the electrodes to the energy sources via an electrical lead circuit. The electrical ports may be configured in a manner allowing an operator to readily reconfigure the device mechanically or through electrical control allowing switching, or may be configured in a fixed manner In some embodiments, an electrical lead circuit is provided which may comprise wires, resistors, and switches and providing an electrical pathway between selected ports of electrical energy sources and electrodes. If the electrical lead circuit contains switches they may be mechanical and controlled by an operator or electronic digital or electronic analog switches controlled by the controller. The electrical lead circuit may include further safety and control circuits including a diode or fuse.

In some embodiments, an electrical monitor is provided which may be configured to collect information on the voltage and/or current at the electrodes (e.g., the voltage produced across two electrodes). This monitor may take the form of at least one of a high-impedance amplifier and an analog-to-digital converter. Physically, the monitor may be a stand-along device or may be part of either electrical energy source or the controller. A preferred electrical monitor has a high input impedance, is isolated form the circuit, and/or employs instrumentation amplifiers. The electrical monitor may include analog or digital feature allowing operation during electrical stimulation by the first electrical energy source and test stimulation by the secondary source, for example filtering, such as either high pass or low pass filtering, or notch filters, blanking amplifier, offset removal, and/or design of voltage range and digitization resolution.

A controller may be provided in some embodiments, which may comprise an electrical microcontroller configured to integrate activities of, for example, the first and second electrical energy sources, and process information collected by the electrical monitor. The controller may process the information from the electrical monitor and may perform any one or more of the following: adjust the output of the first and/or second electrical energy sources, generate a summary that may be stored in a memory (e.g., a hard-disk, database, etc.) and/or may be output on a display. In processing signals, the controller may use algorithms that consider the location of electrodes on a specific body part (e.g., head), and/or consider the specific body part anatomy. The controller may also use the principle of super-position in calculations, including finite element methods and/or model approximations of the head and/or electrodes.

In some embodiments, which may be referred to as the second general embodiment and as "Electrical Potential Tomography", the second electrical energy source may not be required. In some such embodiments, the monitor may use a model (e.g., a FEM model), to decompose the individual potentials at each electrode based on potential generated during stimulation. This can be facilitated by two approaches.

For example, at least one true sentinel electrodes (e.g., of the second type) may be used to detect at least one voltage across an electrode used in stimulation and the sentinel. As the sentinel has no electrode potential, this leaves only the electrode potential of the stimulating electrode being evaluated and any tissue voltage (including scalp voltage/artifact) changes. The latter can be removed by several means, including, for example 1) by assuming they are small relative to the relevant changes of electrode potential; 2) by focusing only on changes where only the electrode potential, not the tissue voltage should change; 3) by using a head model to predict and remove tissue voltages; 4) by using test signal prior (for example SCAN MODE) and/or during (for example secondary stimulation source) stimulation to access the contribution of tissue voltages; 5) by placing the essential electrode in a position with no significant tissue induced voltages, where this position can be determined by placing the true sentinel electrode at sufficient distance from the stimulating electrodes, or can be determined by using a model (as show below) to predict a region with little or no induced voltages.

In some embodiments, at least one of an "equivalent sentinel" may be used. An equivalent sentinel is an electrode which though used in stimulation, and so connected to the first electrical energy source, has little or negligible current. This electrode may then be used as described for the true sentinel. An equivalent sentinel may be generated intentionally, for example, when using multiple current sources in the first electrical energy source, one terminal from each current source may be connected to the same electrodes and stimulation may be applied such that the current at the sentinel electrodes is zero or near zero. Methods described for the true sentinel may also be for the equivalent sentinel.

In some embodiments, an electrode based therapeutic treatment system for stimulating tissue to effect a physiological effect is provided which may comprise a plurality of current sources, each current source having a positive output and a negative output and each being configured to provide a first current, a plurality of stimulating electrodes electrically connected with the plurality of current sources such that at least a pair of the stimulating electrodes share at least one output of at least one of the plurality of current sources, the stimulating electrodes configured to provide electrical energy to tissue of a patient at the first current, at least one sentinel electrode, and a first voltage monitor configured to monitor a first voltage across the at least one sentinel electrode and at least one of the plurality of stimulating electrodes.

In some embodiments, a device for electrical stimulation is provided which may comprise at least two electrodes in contact with the body or tissue, a circuit connected to the two electrodes, a monitor, and a controller having operational thereon computer instructions configured to perform computational processes including at least one of matrix operation, triangulation, and modeling. In such embodiments:

at least one electrical source produces a waveform with at least two components, at least one said components is configured for detection by the monitor and distinguishable by at least one of the computational processes, at least of one of the components of the waveform produces a physiological change;

at least one of the components is configured to interrogate the status of at least one of the electrodes, and the body or tissue, and the circuit is configured to determine which electrodes receive with waveform components.

In some embodiments, an electrode based therapeutic treatment system for stimulating tissue to effect a physiological effect is provided which may comprise a plurality of current sources, each current source having a positive output and a negative output and each being configured to provide a first current. In such embodiments, a plurality of stimulating electrodes may be configured to be placed adjacent tissue, the stimulating electrodes electrically connected with the plurality of current sources such that at least a pair of the stimulating electrodes share at least one output of at least one of the plurality of current sources. The stimulating electrodes may be configured to provide electrical energy to tissue of a patient at the first current. Such embodiments may further include a voltage monitor configured for monitoring the voltage across at least a pair of outputs of at least one of the plurality of current sources. In such embodiments, at least one of the plurality of current sources is configured to supply current at a first distinguishable characteristic from the current supplied by at least one other current source.

Disclosed embodiments of the present disclosure may further include one and/or another of the following features:

- a current source characteristic comprises at least one of a frequency and a phase;
- at least one sentinel electrode is not connected to any of the plurality of current sources;
- a controller configured for at least controlling the output of at least one of the plurality of current sources based upon at least the first voltage;
- a second voltage monitor for monitoring the voltage across at least a pair of outputs of at least one of the plurality of current sources;
- current sources are configured to supply at least a DC current;
- an increase in the first voltage between the at least one sentinel electrode and the at least one stimulating electrode corresponds to an increase in voltage of the at least one stimulating electrode;
- the at least one sentinel electrode comprises a plurality of sentinel electrodes;
- each sentinel electrode is paired with a specific stimulating electrode;
- the first monitor is configured to monitor the voltage between each sentinel electrode and a respective stimulating electrode;
- at least one stimulating electrode is configured to pass electrical energy from the at least one current source to the tissue to effect physiological change;
- a first current source of the plurality of current sources provides current at a first frequency less than or equal to about 100 Hz;
- a second current source of the plurality of current sources provides current at a second frequency distinct from the first frequency;
- the second frequency is less than or equal to about 10 kHz;
- at least one of the plurality of current sources includes a DC component;
- a controller having computer instructions operating thereon configured for receiving information from the first voltage monitor and determining voltage across the at least one sentinel electrode and at least one of the plurality of stimulating electrodes based on a computation model of current flow;
- a computational model includes a representation of the tissue and the position of at least one of the stimulating electrode and the sentinel electrode relative to the tissue;
- computer instructions are further configured to receive anatomical specific information for use by the computation model, where the anatomical specific information can comprise at least MRI;
- computer instructions further configured to perform a test phase at the determined voltage;
- only one first current source is activated during the test phase;
- at least one sentinel electrode comprises either a semi-dry or dry-electrode;
- a plurality of stimulating electrodes comprise two stimulating electrodes and the at least one sentinel electrode comprises a single sentinel electrode;
- current produced by each current source of the plurality of current sources is configured with at least one of a waveform and frequency distinguishable from one another;
- at least two of the current sources are frequency multiplexed;
- at least two of the current sources are time multiplexed; and
- each stimulating electrode is connected to each current source.

Functionality captured by any and all system and device embodiments supported herein also can be repositioned or otherwise claimed as method embodiments, such that, for example, steps carried out by system and device embodiments comprise embodiments of the present disclosure as well.

Moreover, combinations of the above-noted embodiments may also be effected.

DETAILED DESCRIPTION OF SOME OF THE EMBODIMENTS

Figure 1:
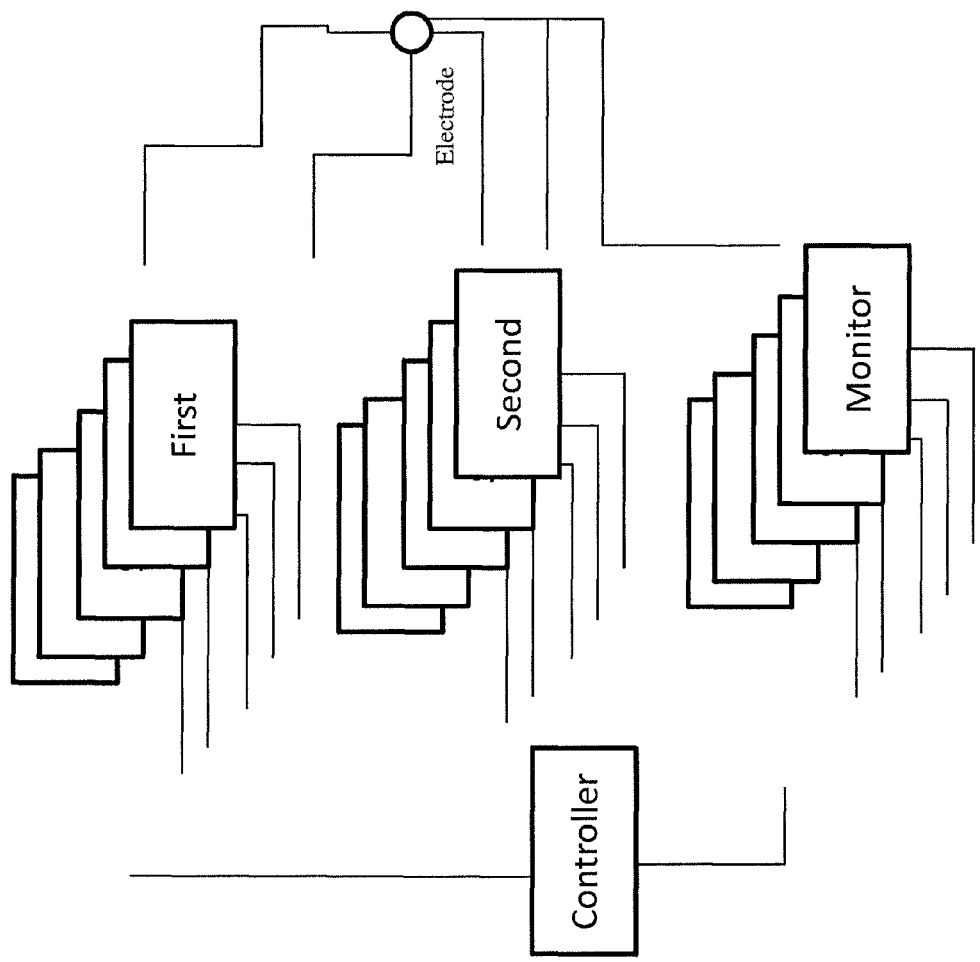
FIG. 1-34 shows schemes of electrode, first stimulation source, second stimulation sources, and monitor connections, according to various embodiments of the present disclosure.
Figure 2:
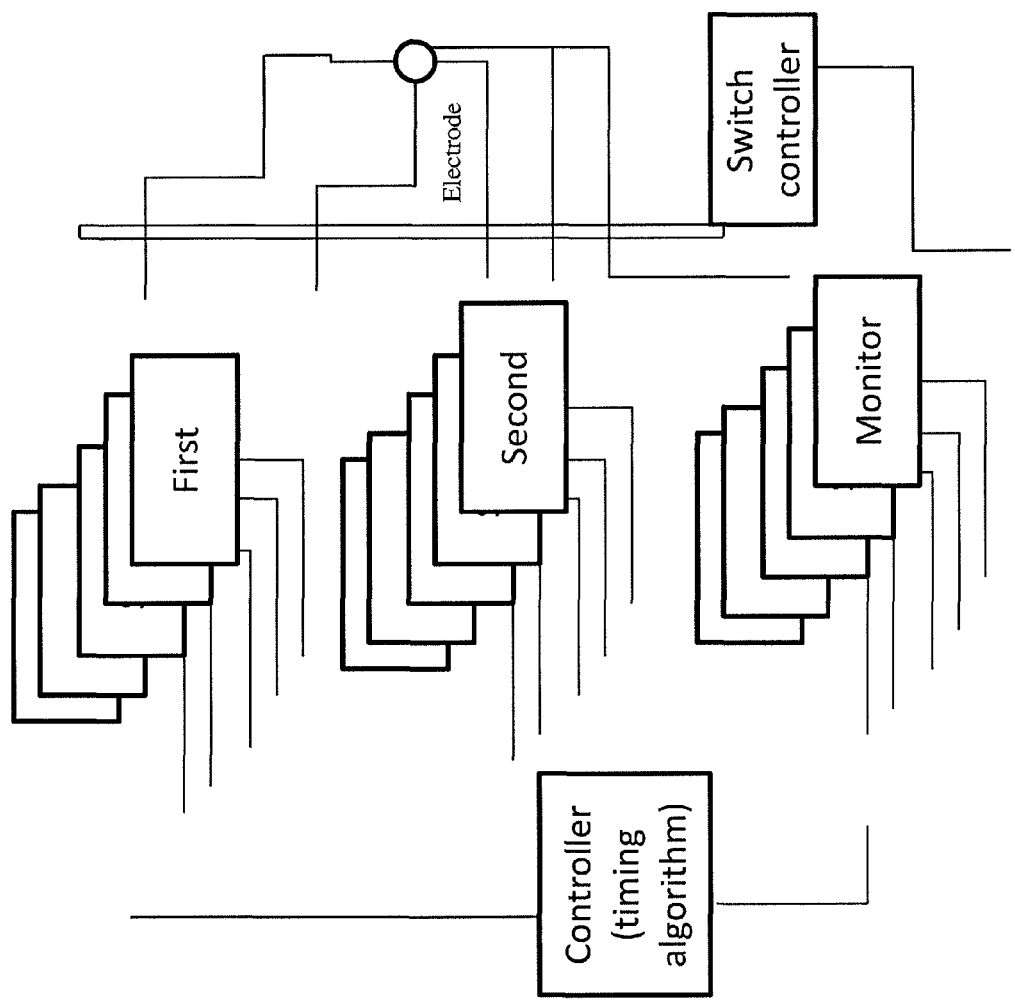

Embodiments according to the Second General Embodiment are described herein, including methods to identify the voltage on at least one reference electrode. Accordingly, a system is provided according to some embodiments where the voltage generated from at least one stimulating electrode is measured relative to at least one sentinel electrode. In such embodiments, at least two stimulating electrodes are used. Scalp voltage generated at the sentinel electrode is subtracted from the voltage measured across the stimulating and sentinel electrode to produce the true stimulating electrode over-potential. The scalp voltage may be determined using at least one of several means. For example: the scalp voltage may be determined at a distance from any stimulating electrodes, such that it is zero, (in the scalp for example selected form 10-20 EEG, or at an extra-cephalic location); it may be predicted based on a priori models, and it may be predicted based on experimental measurements (as in scan mode).

The system may use a scan and stimulation mode, such that in a scan mode, there are two or more stimulating electrodes and at least one sentinel electrode. In the scan mode, the configuration of stimulation and sentinel electrodes may change, for example the electrodes used for stimulating may change. In some embodiments, any and all the electrodes not used for stimulating may be used as sentinel electrodes. The potential measured from the sentinel electrodes during scan mode can be processed, including using a head model, or can be used to parameterize a model, including a head mode. In some embodiments, each electrode is used at least once for stimulation and a plurality of the remaining electrodes not used for stimulation (e.g., which may be all the remaining electrodes) may be used to record. This information may be used to generate an artifact map for the stimulating electrode to each recoding electrode. During stimulation mode, stimulation combined with the current applied at each electrode may be used to estimate the expected artifact voltage at each electrode. This information can be used to detect stimulation faults or to facilitate electrode-potential tomography (for example, by identifying a zero voltage reference or predicting the voltage to subtract for zero reference).

Some Embodiments of the First General Embodiment

In such embodiments, the system can involve three or more electrodes used for stimulation, though those skilled in the art can extend this concept to n electrodes. Therapeutic current is passed between the electrodes for the purpose of inducing a physiological change, for example as change in brain function. The therapeutic current may have a well-defined frequency content (e.g. DC, sinusoid) and/or well-defined temporal pattern (e.g. on/off) such that one may have frequency and/or temporal content that are not included in the therapeutic stimulation. For example, if the therapeutic stimulation is DC current, than AC current may not be included (this may be referred to as a distinct "signature"). The stimulation current may have a certain frequency content where there is little or no stimulation at a one or more specific frequencies, such that those latter frequencies are signature currents. As another example, when the stimulation is off, any signal would be a signature signal.

In a preferred embodiment, the signature signal is not present in any of the stimulating electrodes though variations are considered below. Current or voltage sources generate the stimulating current that is provided to the electrodes as well as additional voltage or current that is in the signature frequency. The current and voltage sources used to generate the therapeutic stimulation may be the same or distinct. Typically, the signature signal will be lower intensity than the stimulating signal or at a frequency of waveform or combination that minimizes the physiological effects of stimulation. For example, frequencies greater than 1 kHz and/or intensities less than 50 µA. Preferably, if more than one signature signal is provided to the electrodes, each signature signal is distinct. For example, one signature signal may be 100 Hz and another signature signal may be 1000 Hz. In some embodiments, both signature signals may be pulses but applied at different times or phases. Whereas the stimulation signal is primarily to induce physiological changes, the signature signal is used primarily to determine the impedance of the electrodes and/or tissue. This may be facilitated by modeling or algorithms.

In some embodiments, three or more electrodes may be used and a substantial (>0.5 mA) DC current may be applied to each of them. In such embodiments, the net current is preferably at or substantially close to zero and some electrodes may have less current or zero current (or near zero). The passage of DC current from each source generates a voltage. That voltage is present not only at the electrodes generating each stimulation, but also at other electrodes, especially proximal electrodes. In addition to DC current, AC current may be applied between pairs of electrodes. In such embodiments, the AC current is applied such that each electrode has at least one AC current applied through it. If there are N electrodes, the number of frequencies can be N, N−1, N/2, N/2+1, N/2−1, or N+1 or a number greater than this. The impedance determined from those AC frequencies is used to determine the impedance of each electrode or each pair of electrodes.

For example, three electrodes are used with 2 mA, −1 mA, and −1 mA DC current applied to the electrodes forming a circuit. A current of 10 HZ, 50 µA is applied between a pair of electrodes, 100 HZ 50 µA is applied between another pair of electrodes, and 1000 HZ 50 µA is applied between the final pair of electrodes such that there is a distinct (signature) frequency applied between each electrode. One can assume that the tissue resistance is in all cases small, the same for each pair, or constant. One can measures the impedance between each pair a I12, I23, I13, where the index indicates between each pair the impedance is measured. If two impedances are high and one is low, it may be concluded that the electrode involved in both high impedance measurements is high.

Use of sentinel or test electrode: Systems according to some embodiment can involve three electrodes where two are used for stimulation and the third is used as a test electrode. Similarly, more stimulation electrodes can be used (for example, 5, 20, or 100) and/or additional test electrodes may be used. The current applied by the stimulating electrodes may all be the same or may be distinct. It may be DC in the range of about 2 mA per electrode, or less. We can illustrate the point for the three-electrode example, though the same principle can be extended to many electrode combinations. A first current is passed between the two stimulating electrodes, for example 2 mA for 20 minutes. At the same time, a second current is passed between one of the stimulating electrodes and the test electrode. For example, pulses at less than 50 µA. This current should have a signature that is distinct from the first current. Whereas the first current is used to induce a change in brain or physiological function, the second current is used to probe the impedance of the system. If the impedance of the test electrode is low (as a result of for example making it large) or is known, than the impedance of the one stimulating electrode can be inferred. In a similar way, a test current can also be passed between the second stimulating electrodes and the test electrode. This second test current may have a signature that is distinct from the stimulating current and/or the first test current. The impedance calculated from both test currents can be used to estimate the resistance of the two active electrodes. In addition, the impedance calculated from both test currents in combination with the impedance calculated from the two stimulation electrodes, can be used to estimate the resistance of the two active electrodes.

Further methods on the use of sentinel electrodes of the second type and information about head anatomy, as well as information of waveforms to use for second energy source are described.

Sentinel electrodes measure scalp voltages. Sentinel electrodes of the second type are not energized by either the primary electrical source or by the second electrical energy source. The following example illustrates the use of sentinel electrodes of the second type.

Analytical models predict brain current flow and have been experimentally validated using a half-skull tank model (Rush & Driscoll 1968). Over the years, analytical approaches have continued to be used (Ferdjallah et al 1996; Saypol et al 1991; Stecker 2005). More recently, spherical-based models (Datta et al 2008; Miranda et al 2006) using finite element methods (FEM) and increasingly detailed gyri-sulci precise Magnetic Resonance Imaging (MRI)—derived high resolution models have been developed (Datta et al 2009; Salvador et al 2010). However, analytical/spherical-based approaches, animal models, resected skulls, and synthetic phantoms are of limited use because of the critical importance of anatomy and material properties. In 1975, a study measured current flow intra-cortically due to DC stimulation in patients undergoing pre-surgical evaluation for epilepsy (Dymond et al 1975). Patient-specific models can retrospectively analyze the success of a given electrode montage (Datta et al 2011) and compared model predictions with patterns of activation revealed by functional MRI (fMRI) signal (Halko et al 2011). As MRI-derived FEM models may be used to characterize clinical electrotherapies (Bikson et al 2010; Dasilva et al 2012; Im et al 2012; Mendonca et al 2011; Parazzini et al 2011; Sadleir et al 2010) as well as design new electrode montages (Borckardt et al 2012). These models and methods described in the prior can be adapted for the use of head models to facilitate signal processing from the electrical monitor as shown in this example.

During transcranial electrical stimulation, electrode configuration and anatomy determine current distribution through the scalp, which is reflected in scalp voltage maps, and which ultimately determine the distribution of the underlying brain current flow. Here we mapped scalp voltages using sentinel electrodes of the second type. To precisely control the applied electrical stimulation, we used high-definition (HD) stimulation electrodes (Minhas et al 2010). HD montages result in distinct scalp surface voltages that are predicted by high-resolution FEM simulations; it would be understood that his analysis can be extended to any form of non-invasive or invasive stimulation. Surface potentials provide insight into the distribution of brain current flow, and can thus be used in the design of effective and specific transcranial stimulation electrode montages.

The first electrical source(s), second electrical source(s), electrodes, and monitor can be connected using the following montages to achieve the objectives of at least some embodiments of the disclosure.

Figure 3:
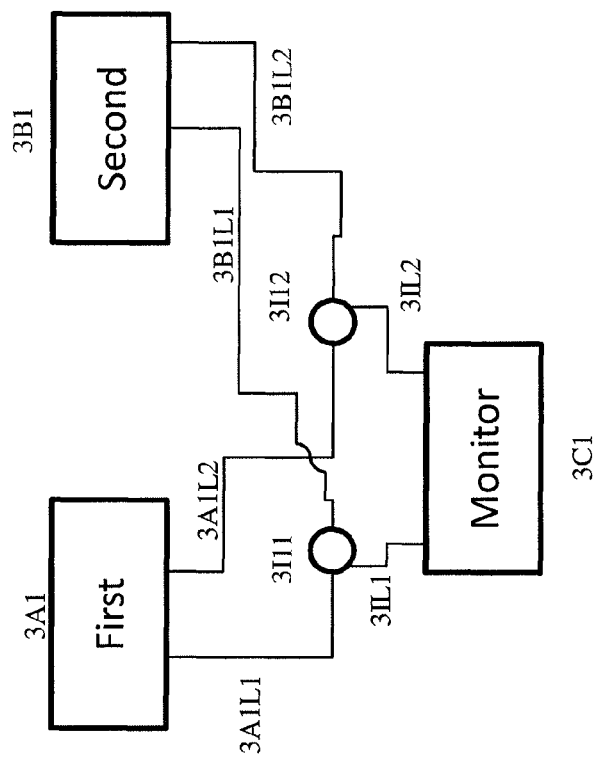

FIG. 3: 3I11 is connected to one port of 3A1 and 3B1 through 3A1L1 and 3B1L1 respectively. Similarly, 3I12 is connected to both 3A1 and 3B1 through 3A1L2 and 3B1L2. Both 3I11 and 3I12 are then connected to 3C1 through 3IL1 and 3IL2 respectively. More generally the number of ports of the first source is equal to the number of ports of the second source, and equal to the number of ports of the monitor, and equal to the number of electrodes. The number of electrodes connected to both of the first source and the second source is equal to the number of ports of the first source and the second source. The number of electrodes not connected to the first source or the second source is equal to the number of ports of the first source minus 2 and to the number of ports of the second source minus 2.

Figure 4:
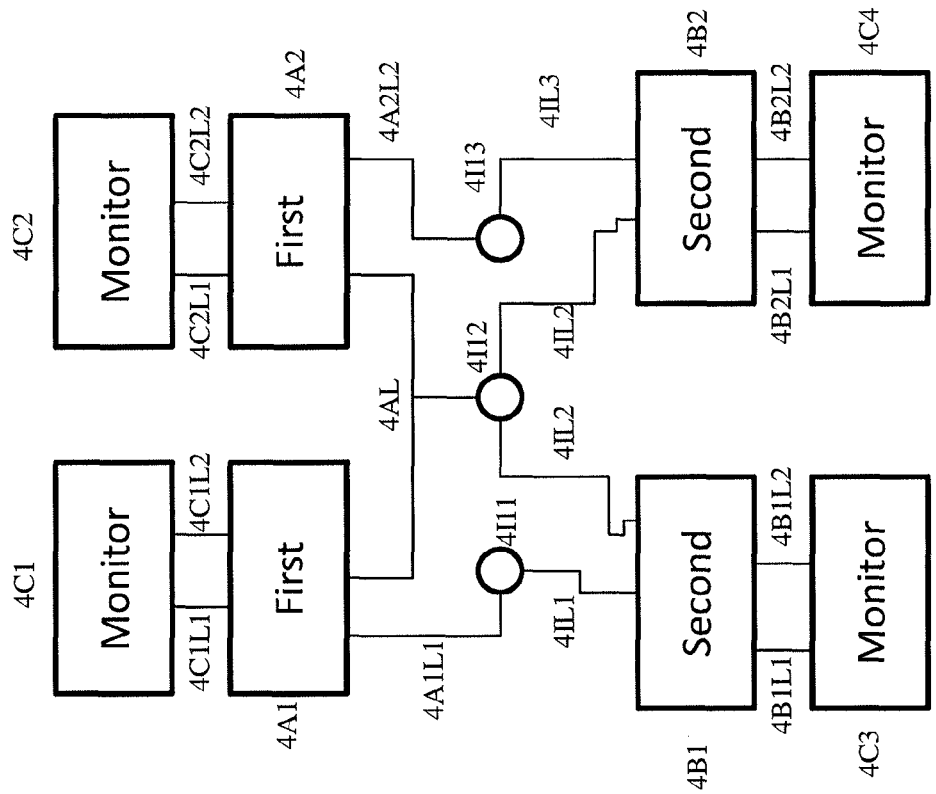

FIG. 4: 4A1 is connected to 4C1 through 4C1L1 and 4C1L2 whereas 4A2 is connected to 4C2 through 4C2L1 and 4C2L2. One port of both 4A1 and 4A2 is connected to 4I12 (common point) through 4AL. The other port of 4A1 is connected to 4I11 through 4A1L1 whereas 4A2 is connected to 4I13 through 4A2L2. 4I11 and 4I12 are then connected to 4B1 through 4IL1 and 4IL2 respectively. Likewise, 4I12 and 4I13 are connected to 4B2 through 4IL2 and 4IL3. 4B1 is connected to 4C3 through 4B1L1 and 4BIL2 whereas 4B2 is connected to 4C4 through 4B2L1 and 4B2L2 respectively. In general, the total number of ports of the first sources is equal to the total number of ports of the second sources, and equal to the number of electrodes minus 1. The total number of electrodes connected to both of the first sources and the second sources is equal to the number of ports of the first sources the number of ports of the second sources plus 1. The number of electrodes not connected to the first sources or the second sources is equal to the total number of ports of the first sources minus 2 and to the total number of ports of the second sources minus 2.

Figure 5:
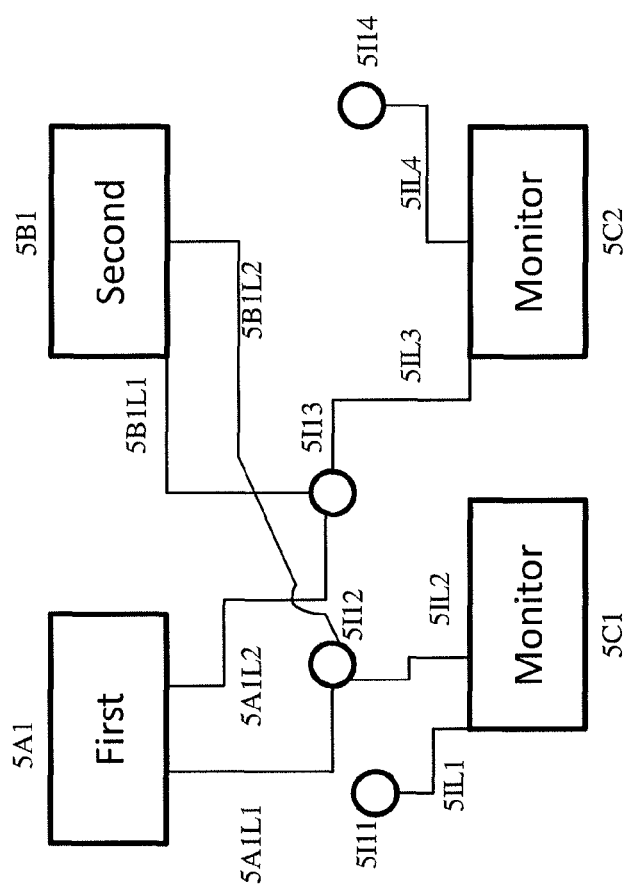

FIG. 5: One port of 5A1 is connected to 5I12 through 5A1L1 and one port of 5B2 is also connected to 5I12 through 5B1L2. The other remaining port of both 5A1 and 5B1 are connected to 5I13 through 5A1L2 and 5B1L1 respectively. 5I11 and 5I12 are then connected to 5C1 through 5IL1 and 5IL2 respectively. Similarly, 5I14 and 5I13 are connected to 5C2 through 5IL3 and 4IL4. Generally, the number of ports of the first source is equal to the number of ports of the second source, and equal to the number of electrodes minus 2. The number of electrodes connected to both the first source and the second source is equal to the number of ports of the first source and the second source. The number of electrodes not connected to the first source or the second source is equal to the number of ports of the first source or the second source.

Figure 6:
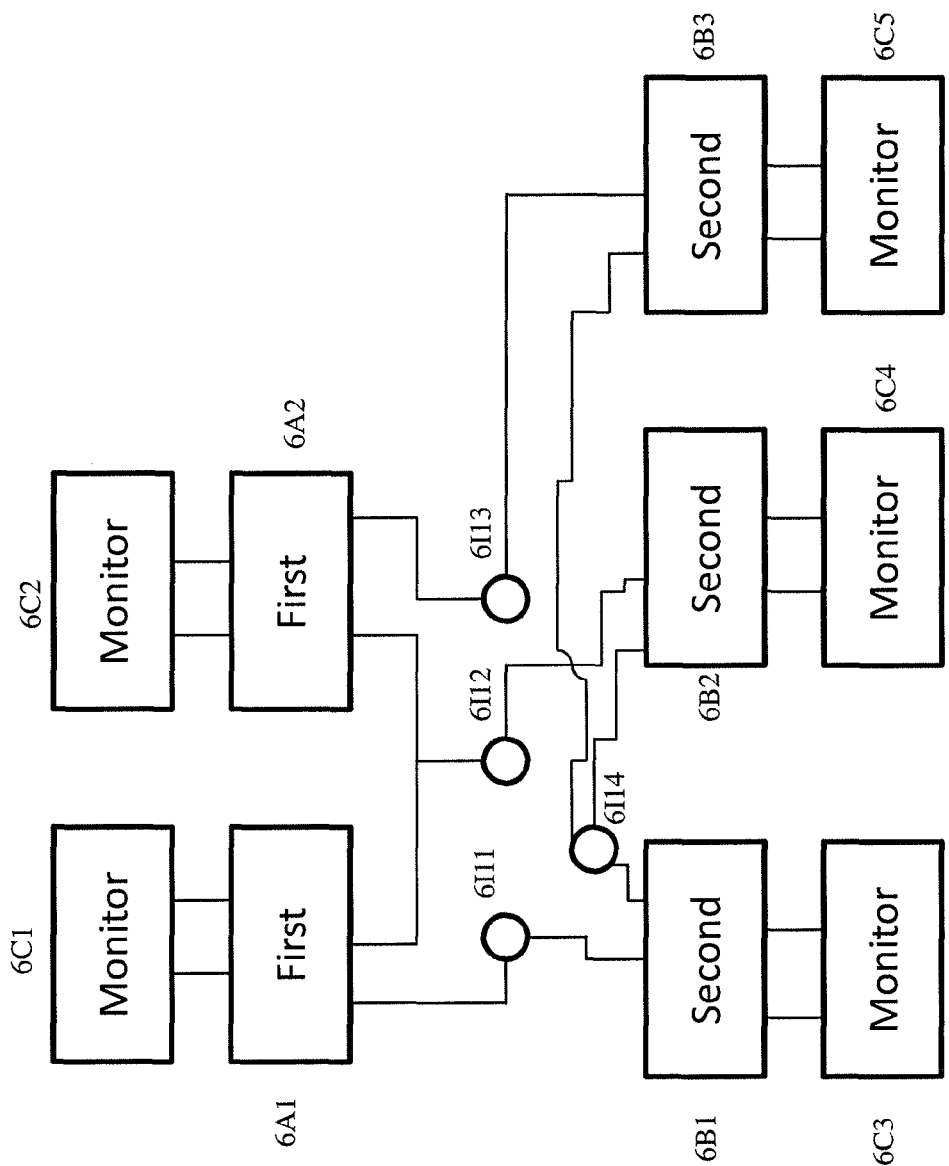

FIG. 6: Both 6A1 and 6A2 are connected to 6C1 and 6C2 respectively. One port of 6A1 and 6A2 are connected together to 6I12 while the other port of 6A1 is connected to 6I11 and that of 6A2 is connected to 6I13. 6I11 and 6I14 are connected to 6B1. 6I12 and 6I14 are connected to 6B2. 6I14 and 6I13 are connected to 6B3. But 6I14 is neither connected to 6A1 not to 6A2. Finally, 6B1, 6B2, 6B3 are connected to 6C3, 6C4 and 6C5 respectively. In general, the number of ports of first source is equal to the number of ports of the monitor, and equal to the number of ports of the second source, and is also equal to the number of electrodes minus 2. More generally, the total number of ports of the first sources is equal to total number of ports of the second sources plus 1, and to the total number of electrodes minus 1. The total number of electrodes connected to the first sources is equal to the total number of electrodes connected to the second sources minus 1. The number of electrodes not connected to the first sources is equal to the number of electrodes connected to both of the first sources and the second sources minus 2. The number of monitors connected to the first sources is equal to the number of monitors connected to the second sources minus 1, and to the total number of electrodes minus 2.

Figure 7:
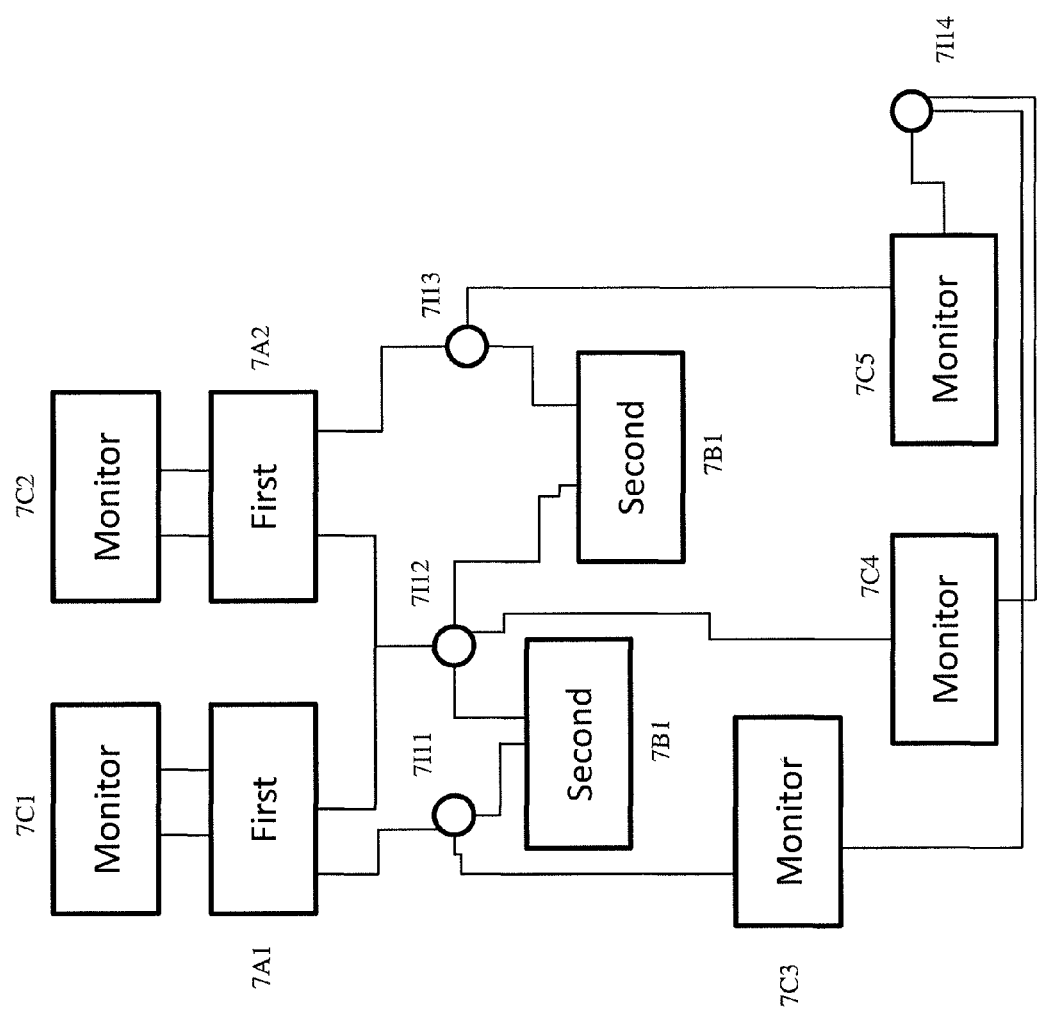

FIG. 7: Both 7A1 and 7A2 are connected to 7C1 and 7C2. One port of each 7A1 and 7A2 are connected to common point 7I12. The other port of 7A1 is connected to 7I11 and that of 7A2 is connected to 7I13. 7I11 and 7I12 are connected to 7B1. 7I11 is also connected to 7C3. 7I13 and 7I12 are connected to 7B1. 7I12 is also connected to 7C4. Similarly 7I13 is also connected to 7C5. 7I14 is connected to 7C3, 7C4, and 7C5 respectively. In general, the total number of ports of the first sources is equal to the total number of ports of the second sources, and to the total number of electrodes minus 2. The number of electrodes connected to the first sources is equal to the total number of electrodes connected to the second source, and to the total number of electrodes connected to the monitors minus 1. The number of electrodes not connected to the first sources or the second sources is equal to the total number of electrodes connected to the first source minus 1.

Figure 8:
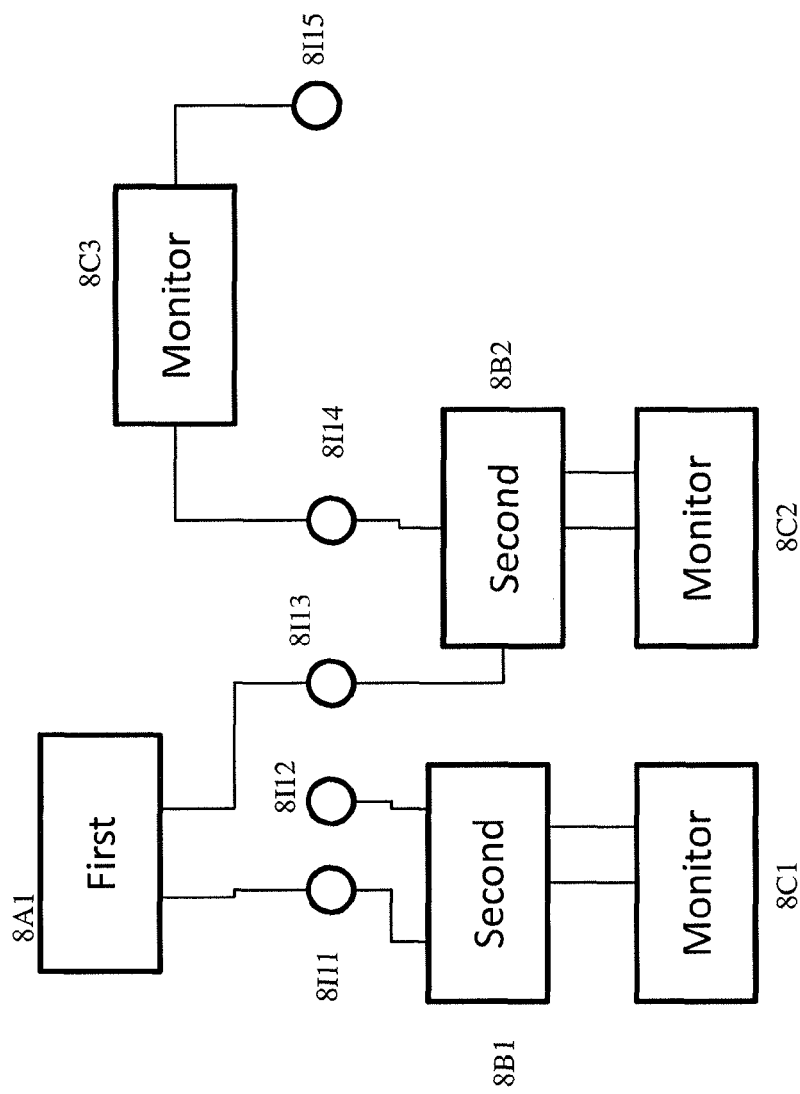

FIG. 8: 8A1 is connected to 8I11 and 8I13. 8I11 and 8I12 are connected to 8B1. 8I13 and 8I14 are connected to 8B2.

8B1 and 8B2 are then connected to 8C1 and 8C2 respectively. 8I14 is also connected to 8C1; which is also connected to 8I15. In general, the total number of ports of the first source is equal to the total number of ports of the second sources minus 2, and equal to the total number of electrodes minus 3. The total number of electrodes connected to both of the first source and the second sources is equal to the number of electrodes connected to the second sources minus 2. The total number of electrodes not connected to the first source is equal to the total number of electrodes connected to the monitor plus 1, and equal to the total number of electrodes connected to the second sources minus 1.

Figure 9:
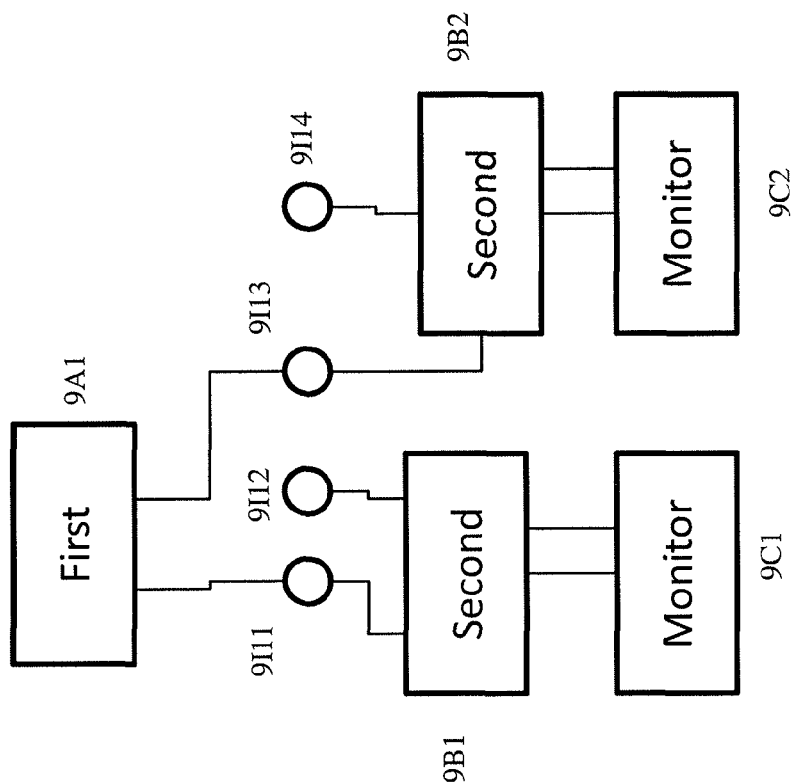

FIG. 9: 9A1 is connected to 9I11 and 9I13. I11 and 9I12 are then connected to 9B1. 9I12 and 9I14 are not connected to 9A1. 9I13 and 9I14 are connected to 9B2. 9B1 and 9B2 are then connected to 9C1 and 9C2. Generally, the total number of ports of the first source is equal to the number of ports of the second source, and equal to the number of electrodes minus 2. The total number of electrodes connected to both of the first source and the second sources is equal to the total number electrodes connected to the second sources minus 2. The total number of electrodes not connected to the first source is equal to the total number of electrodes connected to the first source, and equal to the total number of electrodes connected only to the second sources.

Figure 10:
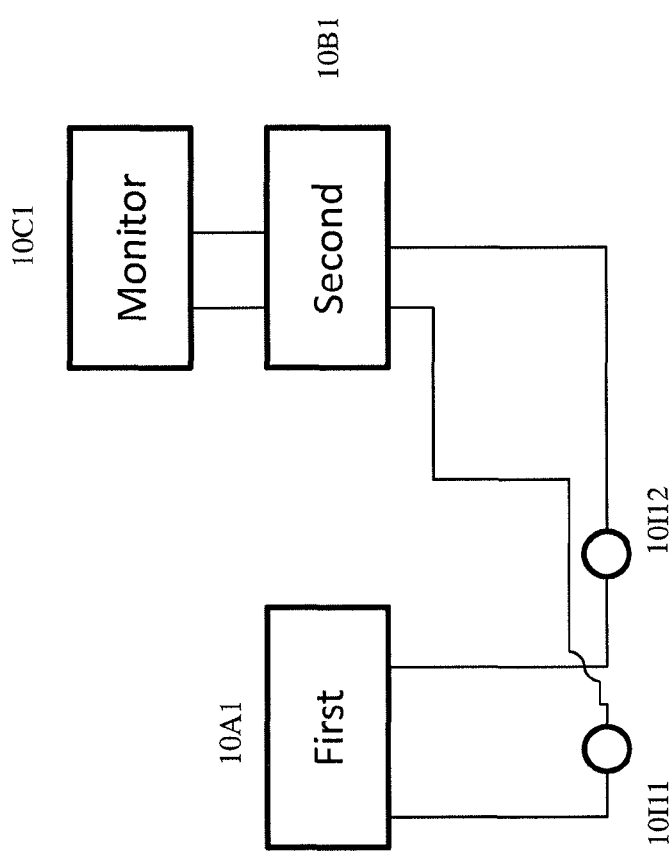

FIG. 10: 10A1 is connected to 10I11 and 10I12. Both 10I11 and 10I12 are then connected to 10B1. 10B1 is connected to 10C1. In general, the number of ports of the first source is equal to the number of port of the second source, and equal to total the number of electrodes. The total number of electrodes connected to both of the first source and the second source is equal to the number of ports of the first source and to the number of ports of the second source. The number of electrodes not connected to the first source is equal to the total number electrodes connected to both of the first and the second source minus 2.

Figure 11:
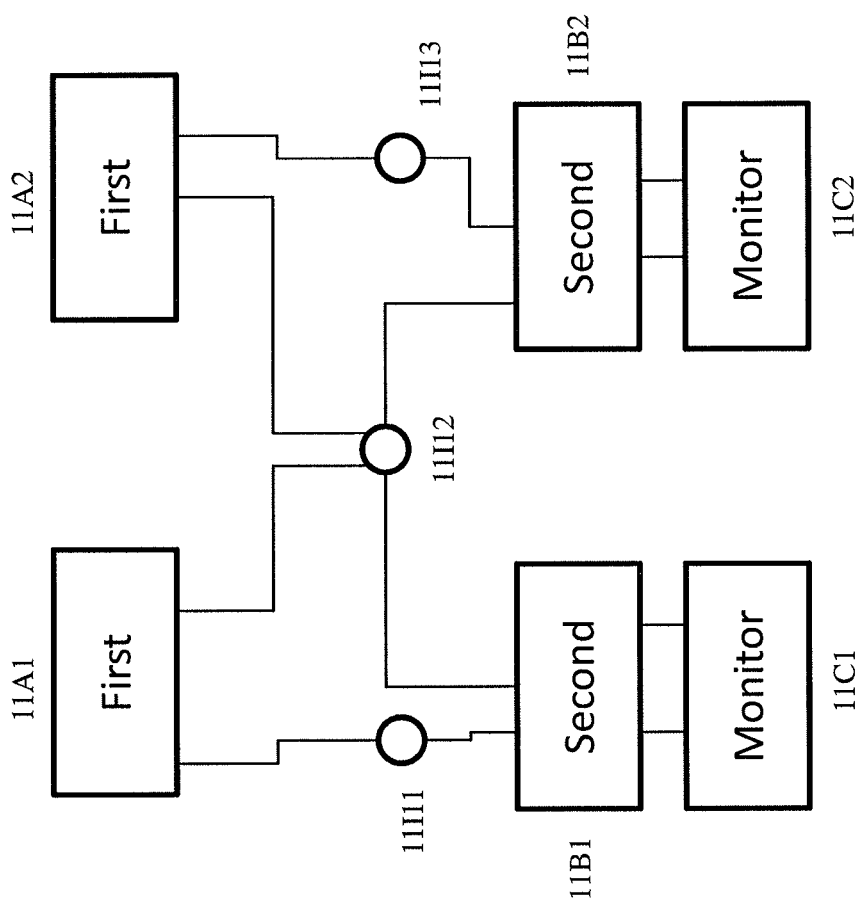

FIG. 11: One port of both 11A1 and 11A2 are connected to 11I12. The other port of 11A1 is connected to 11I11 while the other port that of 11A2 is connected to 11I13. 11I12 and 11I11 are then connected to 11B1 which is also connected to 11C1. 11I12 and 11I13 are connected to 11B2 which is also connected to 11C2. In general, the total number of ports of the first sources is equal to the total number of ports of the second sources, and equal to the total number of electrodes minus 1. The total number of electrodes connected to both of the first sources and the second sources is equal to the total number of ports of the first and the second sources. The total number of electrodes not connected to the first sources or the second sources is equal to the total number of electrodes connected to both of the first and the second sources minus 3.

Figure 12:
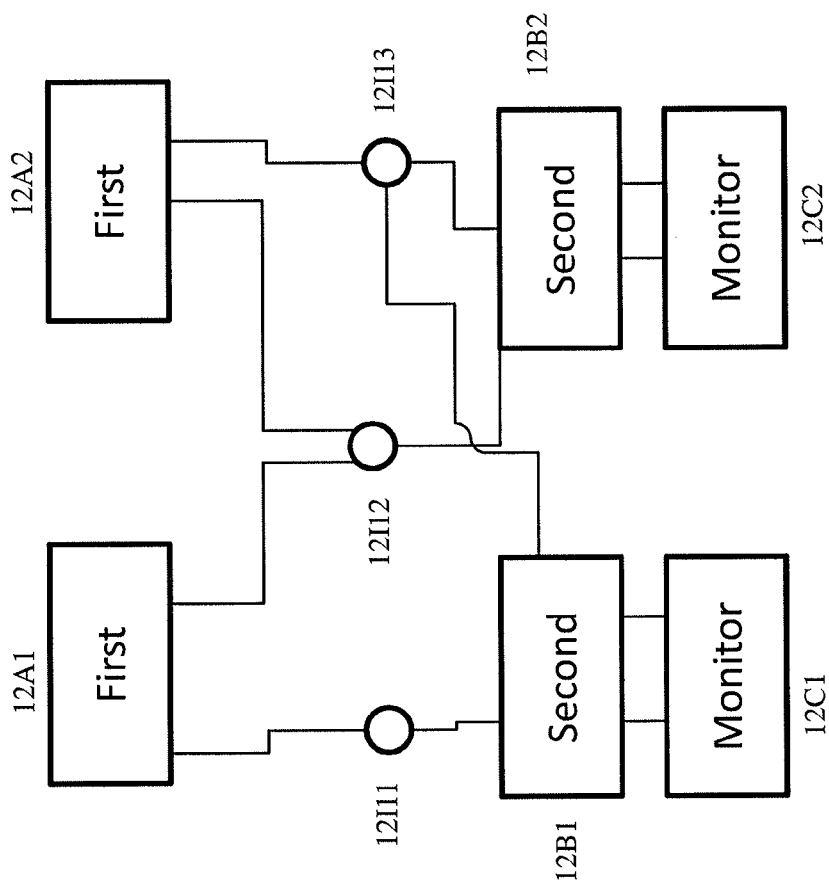

FIG. 12: One port of both 12A1 and 12A2 are connected to 12I12. The other port of 12A1 is connected to 12I11 while the other port that of 12A2 is connected to 12I13. 12I12 and 12I13 are then connected to 12B1 which is also connected to 12C1. 12I12 and 12I13 are connected to 12B2 which is also connected to 12C2. Generally, the total number of ports of the first sources is equal to the total number of ports the second sources plus 1, and equal to the total number of electrodes. The total number of electrodes connected to the first sources is equal to the total number of electrodes connected to the second sources. The total number of electrodes not connected to the first sources or the second sources is equal to the total number of electrodes connected to both of the first sources and the second sources minus 3.

Figure 13:
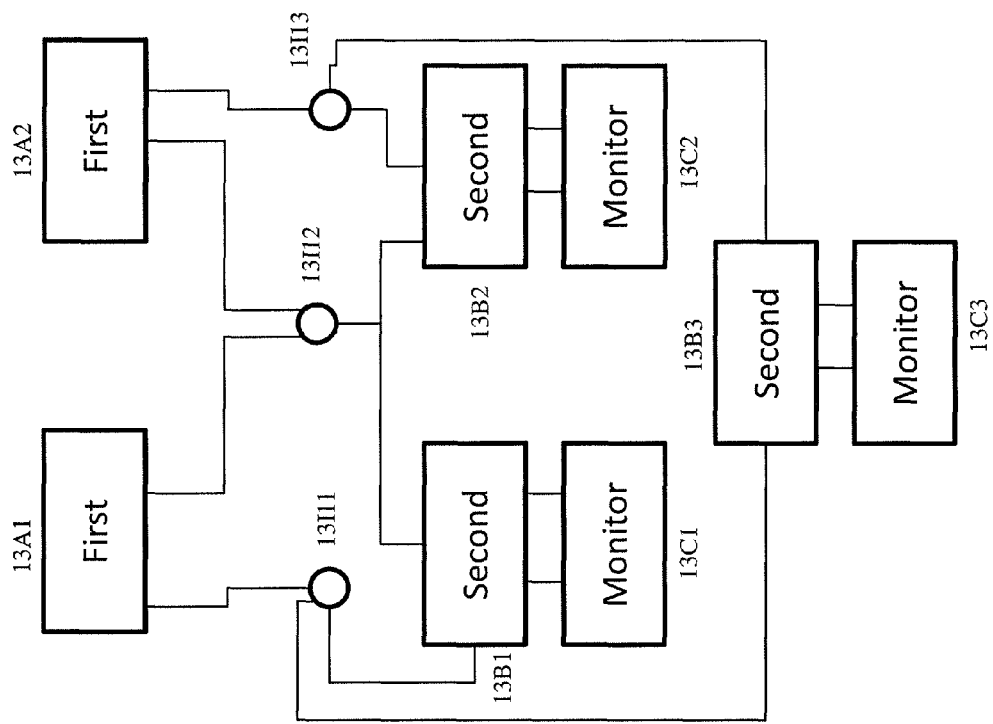

FIG. 13: One port of both 13A1 and 13A2 are connected to 13I12. The other port of 13A1 is connected to 13I11 and that of 13A2 is connected to 13I13. 13I11 and 13I12 are connected to 13B1. 13I11 is also connected to 13B3. 13I12 and 13I13 are connected to 13B2. 13I13 is also connected to 13B3. B1, B2, B3 are connected to 13C1, 13C2 and 13C3 respectively. Generally, the total number of ports of the first sources is equal to the number of ports of the second source, and equal to the total number of electrodes minus 1. The total number of electrodes connected to both of the first sources and the second sources is equal to the total number of ports of the first sources and to the total number of ports of the second sources. The total number of electrodes not connected to the first sources or the second sources is equal to the total number of electrodes connected to the first sources minus 3 and equal to the total number of electrodes connected to the monitors.

Figure 14:
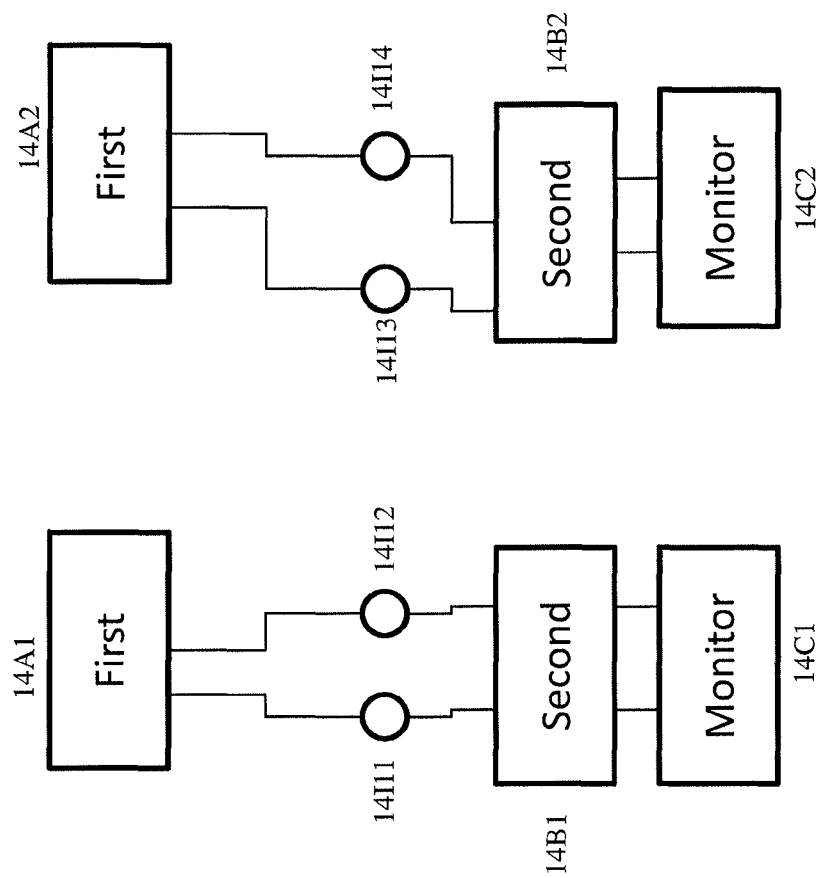

FIG. 14: 14A1 is connected to 14I11 and 14I12 which are further connected to 14B1 and 14C2. Similarly, 14A2 is connected to 14I13 and 14I14 which are connected to 14B2 and 14C2 in an order. In general, the second set up is a replication of the first set up. The total number of ports of the first sources is equal to the total number of ports of the second sources and equal to the total number of electrodes. The total number of electrodes connected to the first source and is equal to the total number of ports of the first source. The total number of electrodes not connected to the first source is equal to the total number of ports of the second source minus 2.

Figure 15:
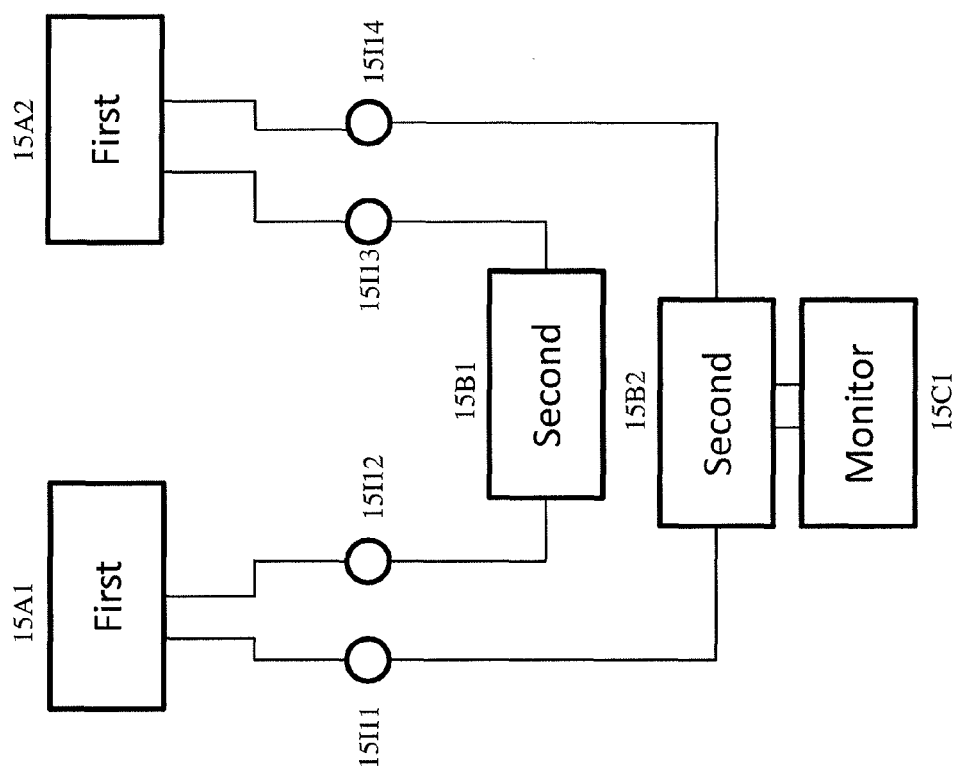

FIG. 15: 15A1 is connected to 15I11 and 15I12 whereas 15A2 is connected to 15I13 and 15I14. 15I11 and 15I14 are both connected to 15B2. 15I12 and 15I13 are connected to 15B1. 15B2 is then connected to 15C1. Generally, the total number of ports of the first sources is equal to the total number of ports the second sources and equal to the total number of electrodes. The total number of electrodes connected to both of the first sources and the second sources is equal to the total number of ports of the first sources and to the total number of ports of the second sources. The total number of electrodes not connected to the first sources or the second sources is equal to the total number of ports of the first sources minus 2, and equal to the total number of ports of the second sources minus 2.

Figure 16:
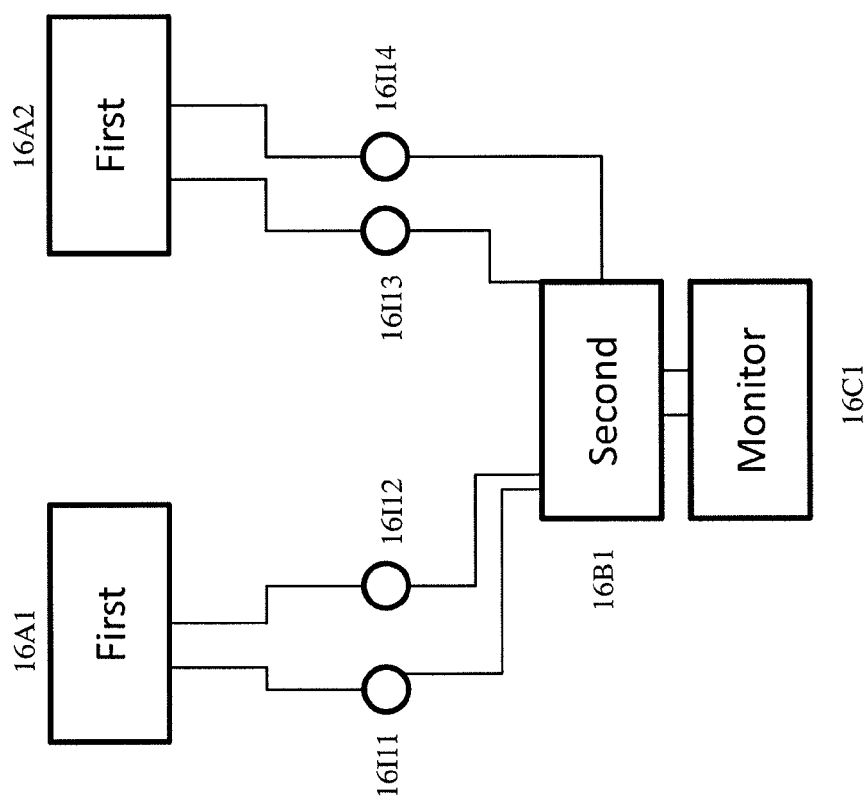

FIG. 16: 16A1 is connected to 16I11 and 16I12 and 16A2 is connected to 16I13 and 16I14. 16I11 and 16I12 are further connected to 16B1. Similarly, 16I13 and 16I14 are connected to 16B1 too. 16B1 is then connected to 16C1. In general, the total number of ports of the first sources is equal to the total number of ports of the second source and equal to the total number of electrodes. The total number of electrodes connected to both of the first sources and the second source is equal to the number of ports of the first sources and equal to the number of ports of the second source. The number of electrodes not connected to the first sources or the second source is equal to the number of ports of the first sources minus 4 and equal to the number of ports of the second source minus 4.

Figure 17:
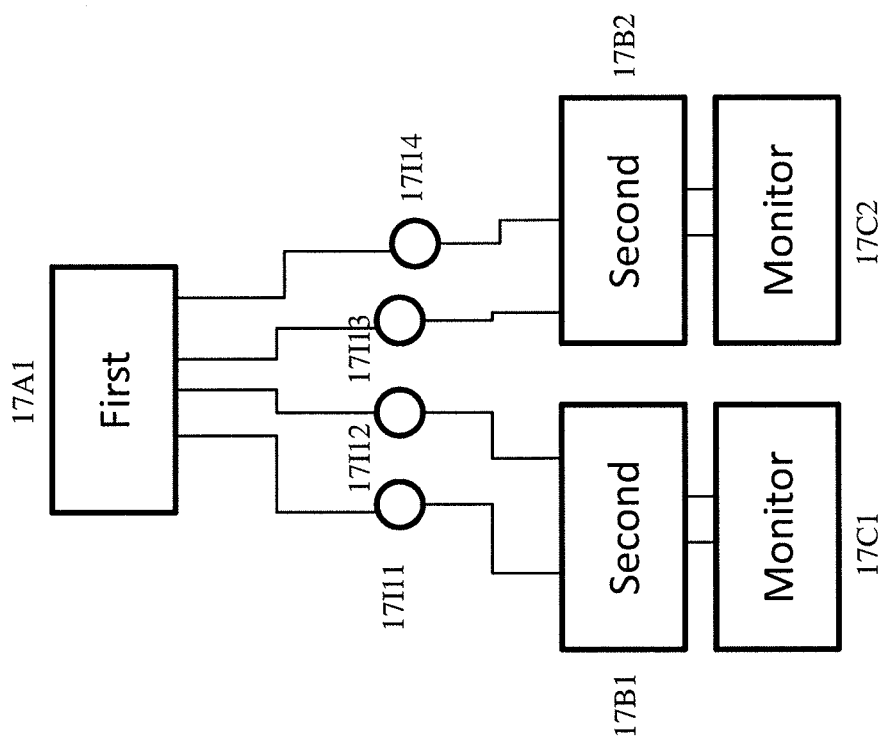

FIG. 17: 17A1 is connected to 17I11, 17I12, I13 and 17I14. 17I11 and 17I12 are connected to 17B1 whereas 17I13 and 17I14 are connected to 17B2. 17B1 and 17B2 are then connected to 17C1 and 17C2 respectively. Generally, the total number of ports of the first source is equal to the total number of ports of the second sources and equal to the total number of electrodes. The total number of electrodes connected to both of the first source and the second sources is equal to the number of ports of the first source and equal to the number of ports of each of the second sources. The number of electrodes not connected to the first source or the second sources is equal to the number of ports of the first source minus 4 and equal to the number of ports of the second sources minus 4.

Figure 18:
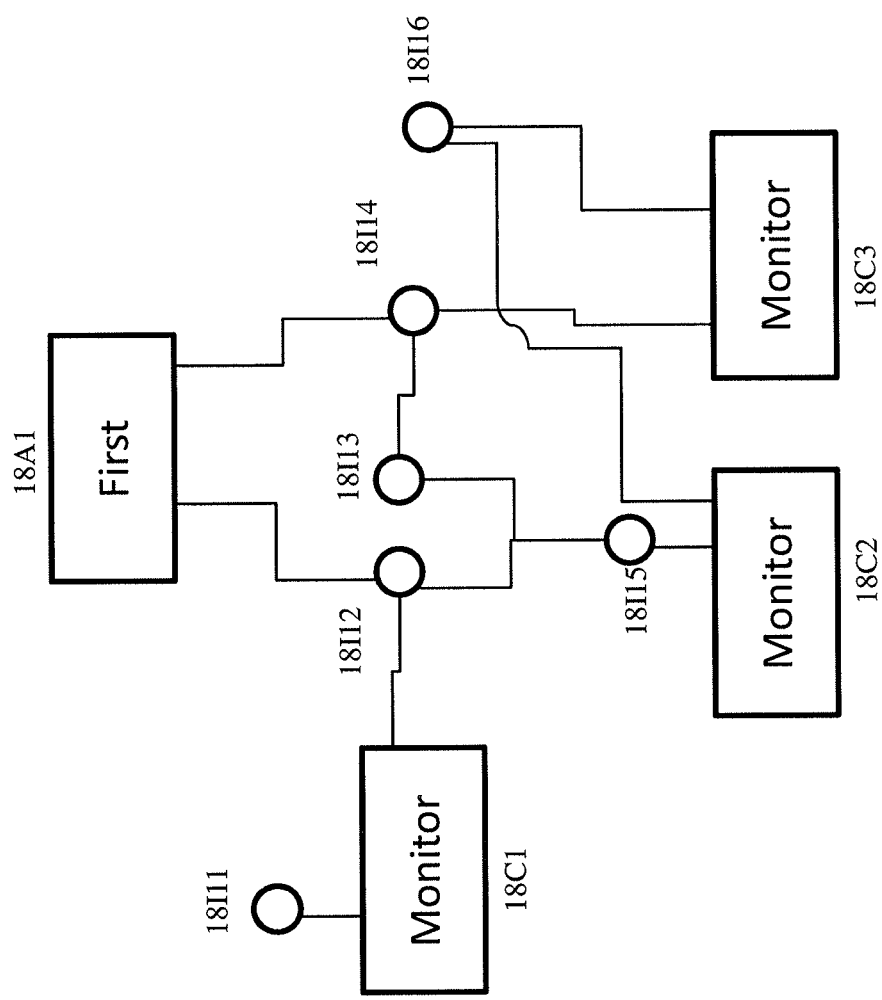

FIG. 18: 18A1 is connected to 18I12 and 18I14. 18I11 is connected to 18C1 but not connected to 18A1. 18I12 is connected to 18I15 and 18I12. 18I13 is connected to 18I14 and 18I15. 18I16 is not connected to 18A1 but is connected to 18C2 and 18C3. 18I14 is also connected to 18C3. 18I15 is connected to 18C2. Generally, the total number of ports of the first source is equal to the number of ports of the monitor and equal to the total number of electrodes minus 4. The total number of electrodes connected to the first source is equal to the total number of electrodes connected to both of the first source and the monitors minus and equal to the total number of electrodes connected to the monitors minus 3. The number of electrodes not connected to the first source is equal to the number of ports of the first source plus 2 and equal to the total number of electrodes connected only to the monitors.

Figure 19:
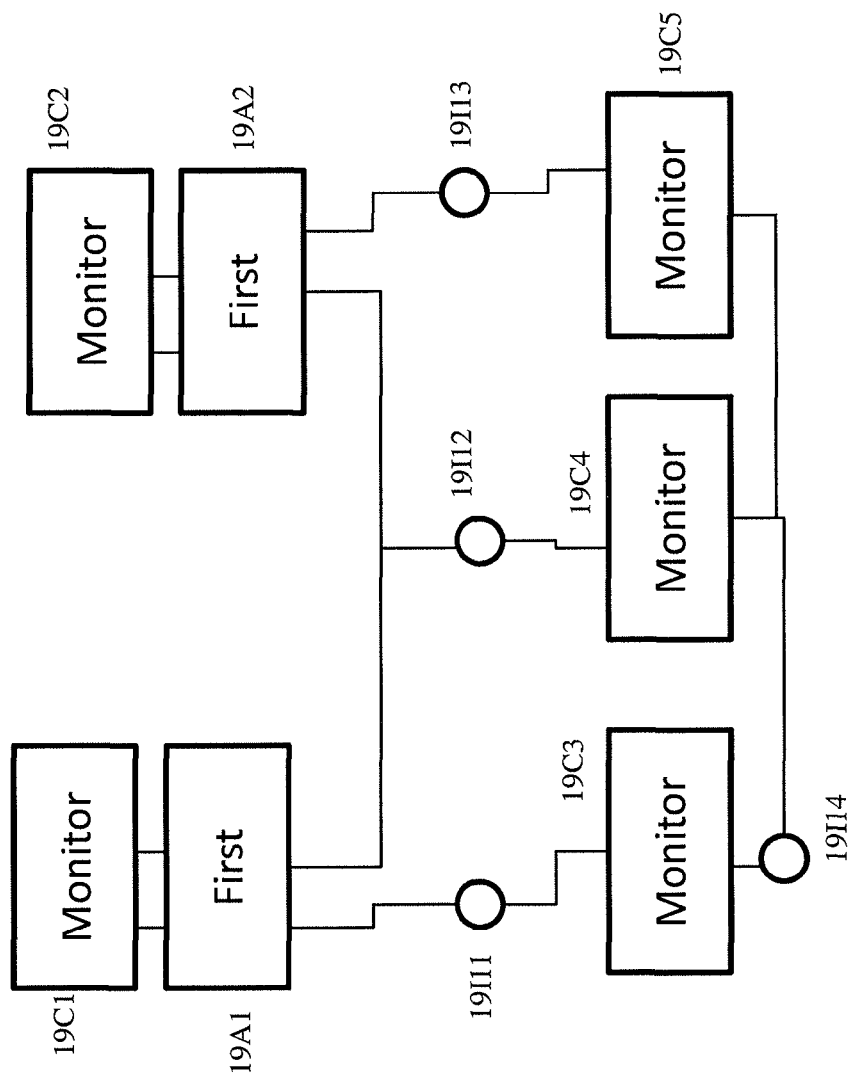

FIG. 19: 19A1 and 19A2 are connected to 19C1 and 19C2 respectively. One port of 19A1 and 19A2 are connected to 19I12. The other port of 19A1 and 19A2 are connected to 19I11 and 19I13 respectively. 19I11 and 19I14 are connected to 19C3. 19I14 and 19I12 are connected to 19C4 and 19I14 and 19I13 are connected to 19C5. More generally, the total number of ports of the first sources is equal to the total number of ports of the monitors minus 1 and equal to the total number of electrodes minus 1. The total number of electrodes connected to both of the first sources and monitors is equal to the number of ports of the first sources and equal to the number of ports of the monitors minus 1. The total number of electrodes not connected to the first sources is equal to the total number of electrodes connected to the monitors minus 3 and to the total number of electrodes connected to the first sources minus 2.

Figure 20:
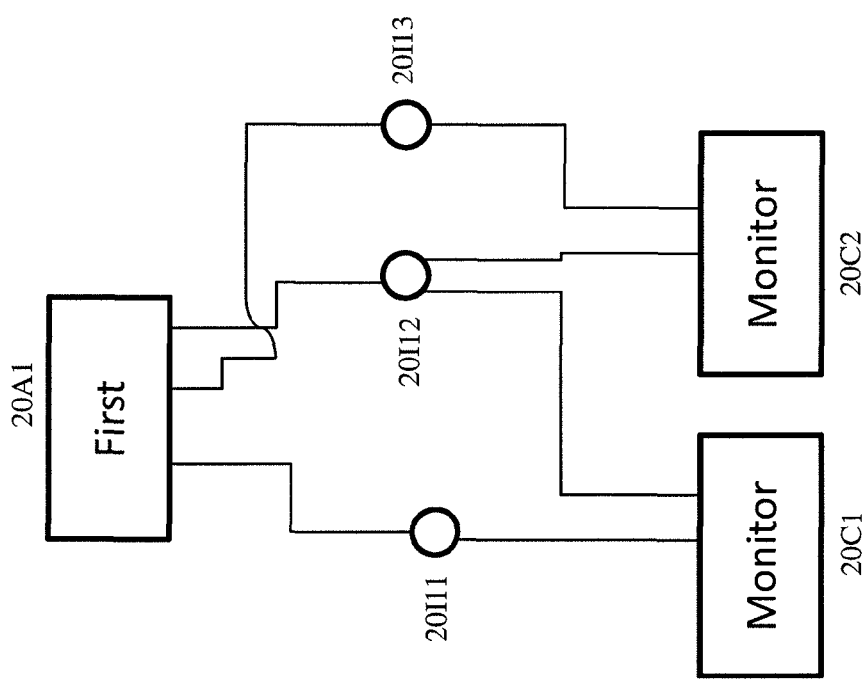

FIG. 20: 20A1 is connected to 20I11, 20I12 and 20I13. 20I11 and 20I12 are connected to 20C1 while 20I12 and 20I13 are connected to 20C2. Generally, the total number of ports of the first source is equal to the total number of ports of the monitors and equal to the number of electrodes. The total number of electrodes connected to both of the first source and the monitors is equal to the total number of ports of the first source. The total number of electrodes not connected to the first source or the monitors is equal to the total number of ports of the first source minus 3 and the total number of ports of the monitors minus 3.

Figure 21:
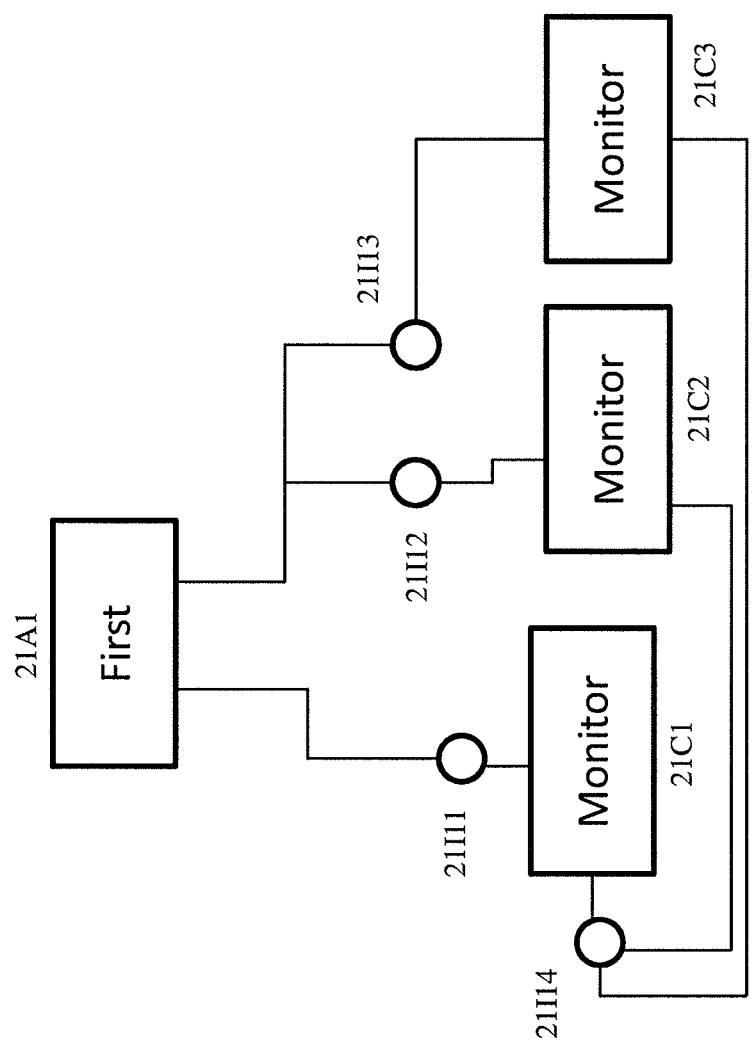

FIG. 21: One port of 21A1 is connected to 21I11 while the other port is further divided into 21I12, 21I13. 21I14 and 21I11 are connected to 21C1 but is not connected to 21A1. Likewise, 21I14 and 21I12 & 21I14 and 21I13 are connected to 21C2 and 21C3 respectively. Generally, the total number of ports of the first source is equal to the total number of ports of the monitors minus 2 and equal to the total number of electrodes minus 2. The total number of electrodes connected to both of the first source and the monitors is equal to the total number of ports of the first source plus 1 and to the total number of ports of the monitors minus 1. The total number of electrodes not connected to the first source is equal to the total number electrodes connected to the monitors minus 3.

Figure 22:
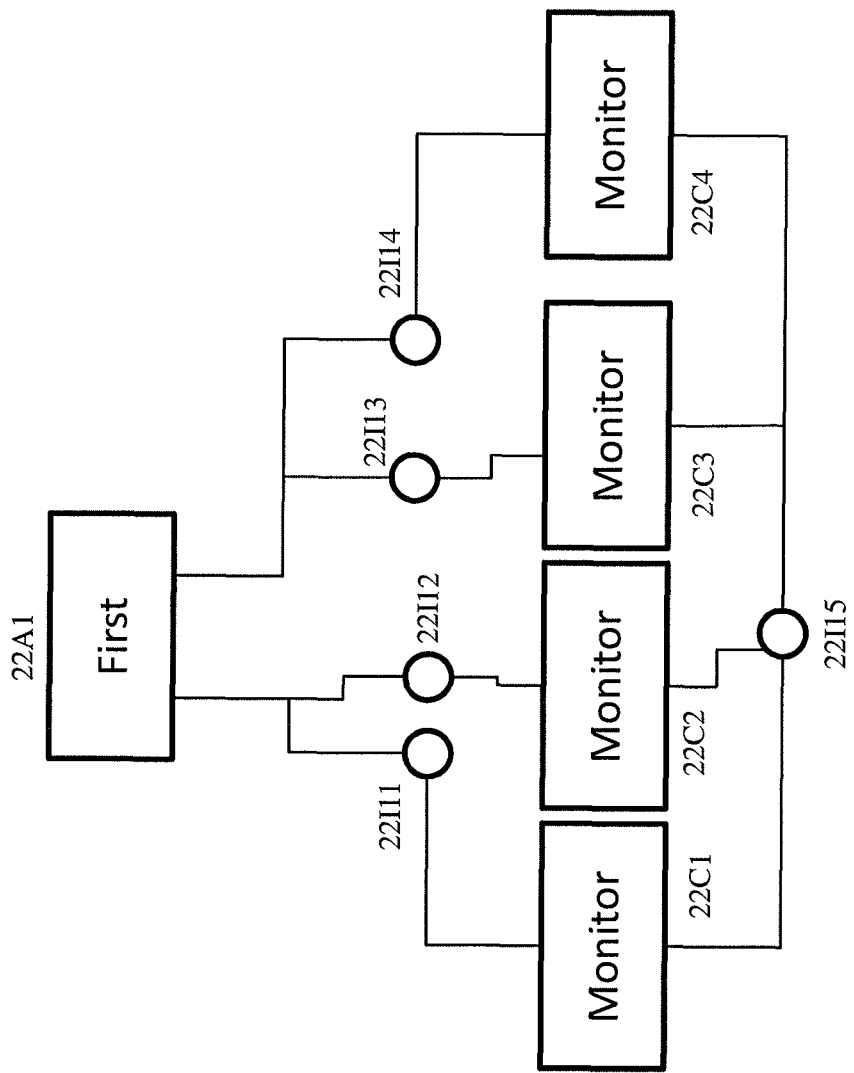

FIG. 22: One port of 22A1 is divided into 22I11 and 22I12 whereas the other port is also divided into 22I13 and 22I14. 22I15 is not connected to 22A1. 22I15 and 22I11, 22I12, 22I13 and 22I14 are connected to 22C1, 22C2, 22C3 and 22C4 respectively. Generally, the total number of ports of the first source is equal to the total number of ports of the monitors minus 3 and equal to the total number of electrodes minus 3. The total number of electrodes connected to both of the first source and the monitors is equal to the number of ports of the first source plus 2 and to the total number of ports of the monitors minus 1. The total number of electrodes not connected to the first source is equal to the number of electrodes connected to the monitors minus 4.

Figure 23:
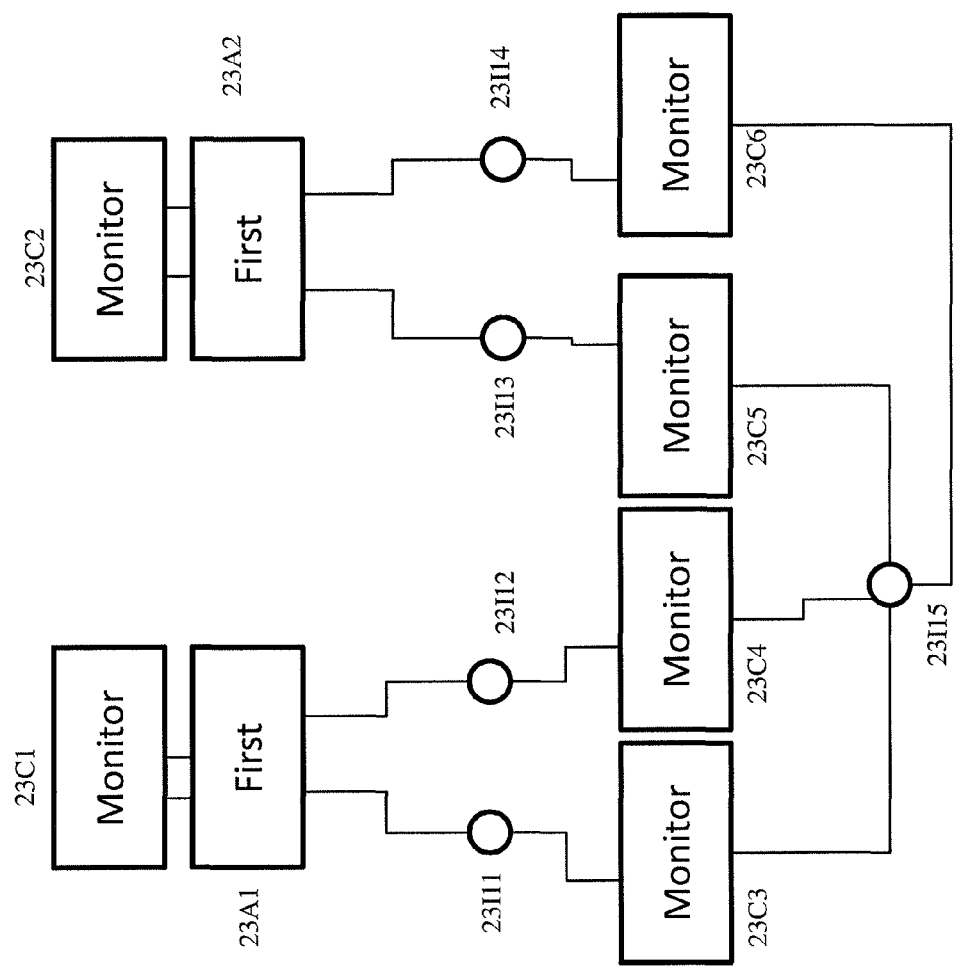

FIG. 23: 23A1 and 23A2 are connected to 23C1 and 23C2. One port 23A1 is connected to 23I11 whereas the other one is connected to 23I12. One port of 23A2 is connected to 23I13 whereas the other was connected to 23I14. 23I11 and 23I15, 23I12 and 23I15, 23I13 and 23I15 and 23I14 and 23I15 are connected to 23C3, 23C4, 23C5 and 23C6 respectively. 23I1115 is neither connected to 23A1 nor to 23A2. Generally, the total number of ports of the first sources is equal to the number of ports of the monitors minus 1 and equal to the total number of electrodes minus 1. The total number of electrodes connected to both of the first sources and the monitors is equal to the total number of ports of the first sources and to the total number of ports of the monitors minus 1. The total number of electrodes not connected to the first source is equal to the total number of ports of the first sources minus 3 and to the total number electrodes connected to the monitors minus 4.

Figure 24:
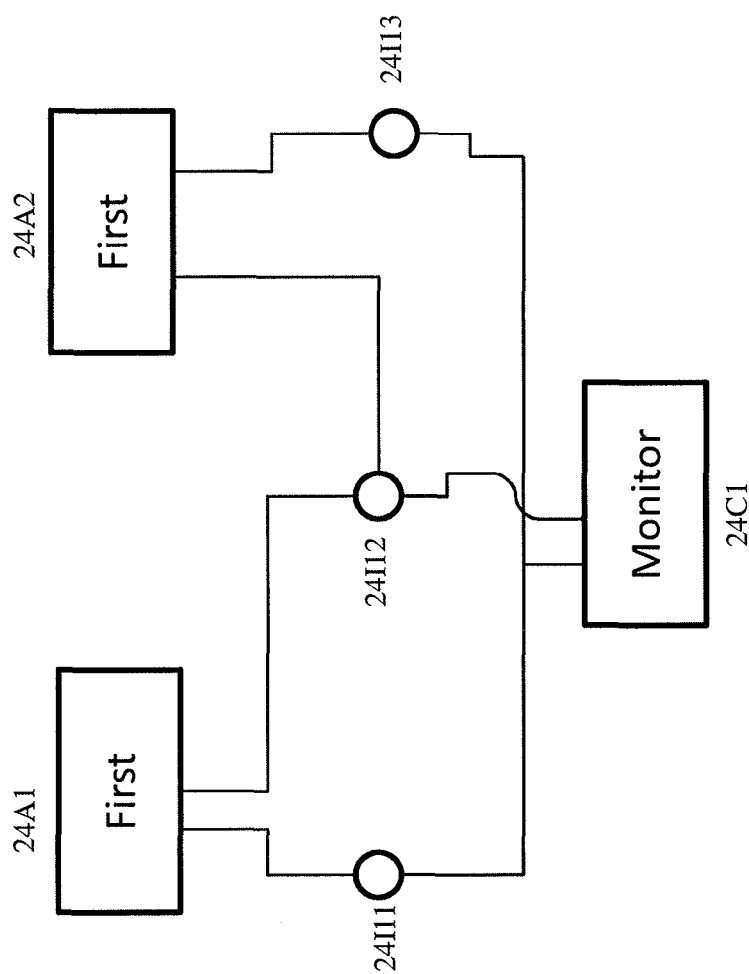

FIG. 24: 24A1 is connected to 24I11 and 24I12. 24A2 is connected to 24I12 and 24I13. 24I11 and 24I13 are connected to 24C1 also 24I12 is connected to 24C1. In general, the total number of ports of the first sources is equal to the total number of ports of the monitor plus 1 and equal to the total number of electrodes. The total number of electrodes connected to both of the first sources and the monitor is equal to the total number of ports of the first sources. The total number of electrodes not connected to the first sources or the monitor is equal to the total number of ports of the first sources minus 3 and to the total number of ports of the monitor minus 2.

Figure 25:
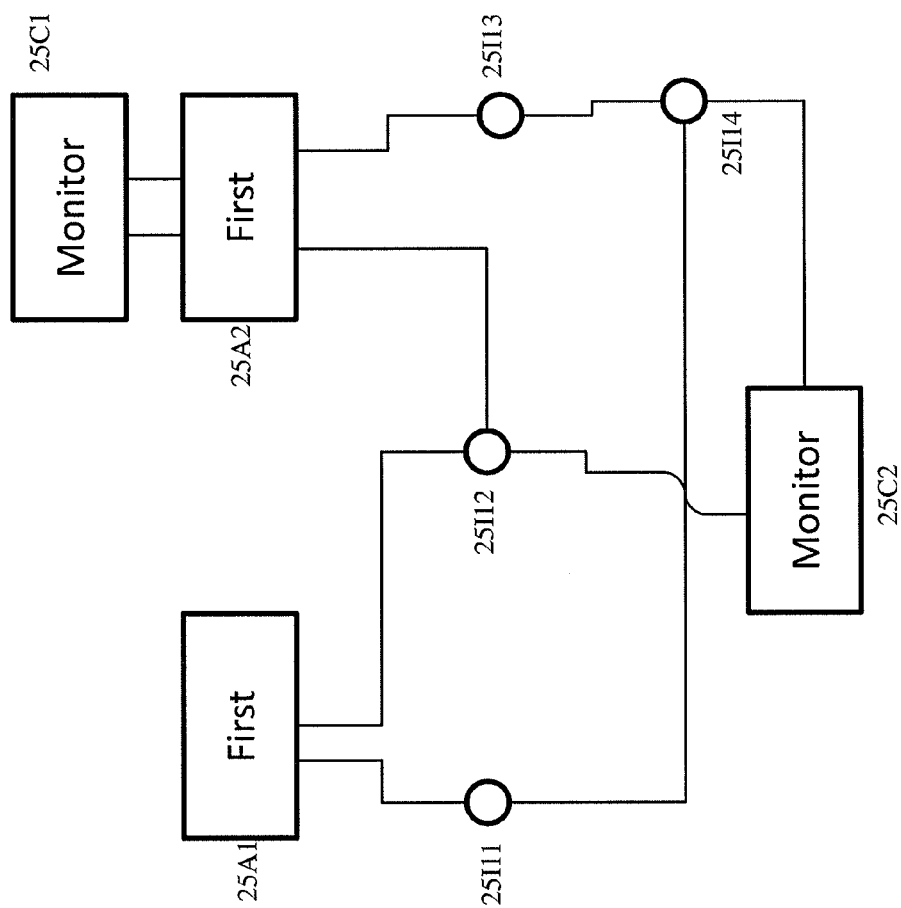

FIG. 25: 25A1 is connected to 25I11 and 25I12. 25A2 is connected to 25C1, 25I12 and 25I13. 25I11 and 25I13 are connected to 25I14. 25I14 is not connected to 25A1 or 25A2. 25I12 and 25I14 are further connected to 25C2. Generally, the total number of ports of the first sources is equal to the total number of ports of the monitor plus 1 and equal to the total number of electrodes minus 1. The total number of electrodes connected to both of the first sources and the monitor is equal to the total number of ports of the first sources plus 1, and to the total number of ports of the monitor plus 2. The total number of electrodes not connected to the first sources is equal to the total number of ports of the first sources minus 3.

Figure 26:
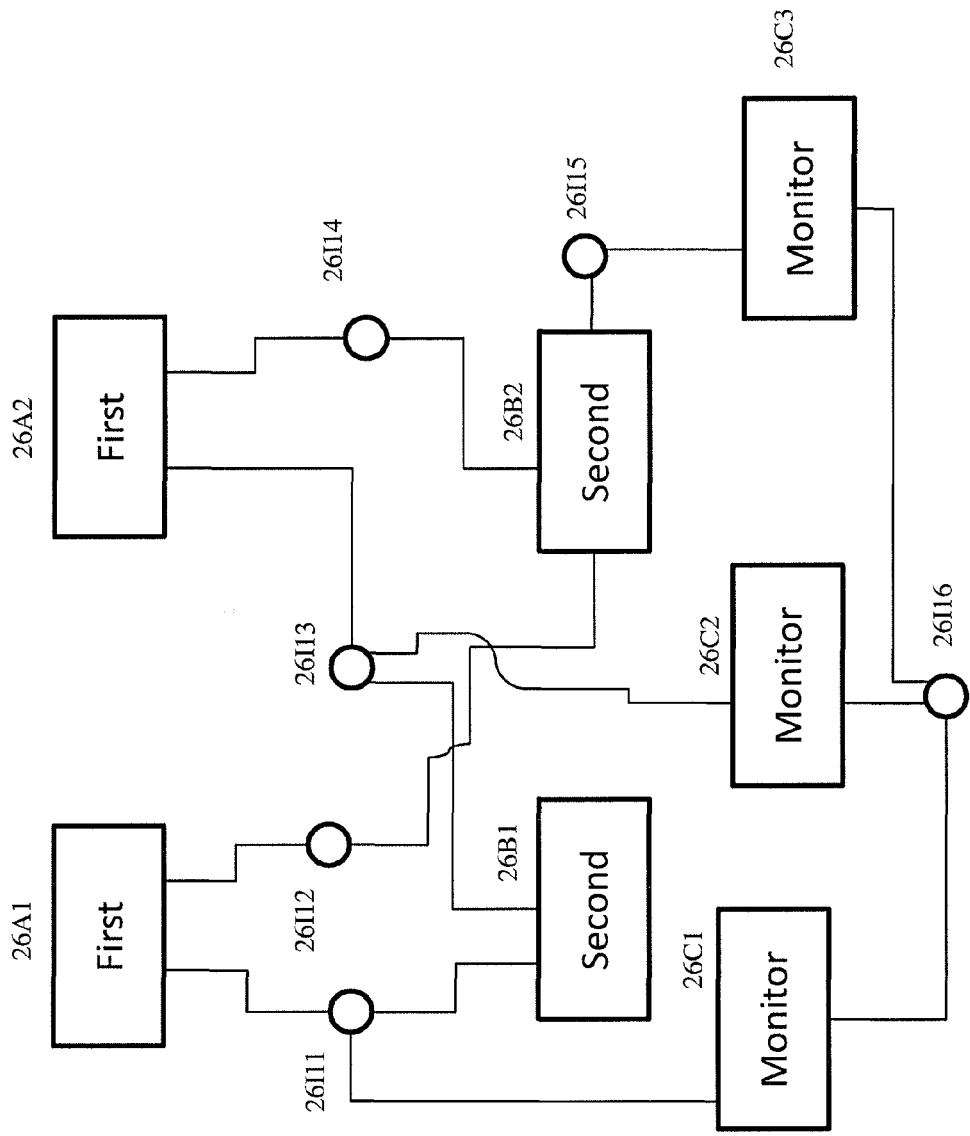

FIG. 26: 26A1 is connected to 26I11 and 26I12 whereas 26A2 is connected to 26I13 and 26I14. 26I11 and 26I13 are connected to 26B1 and 26I12 and 26I14 are connected 26B2. 26I14 and 26I13 are connected to 26C2. 26I16 and 26I11 are connected to 26C1. 26I15 and 26I16 are not connected to 26A1 or 26A2. 26I16 and 26I13 are connected to 26C2. 26I15 and 26I16 are connected to 26C3. Generally, the total number of ports of the first sources is equal to the number of ports of the second sources minus 1and equal to the total number of electrodes minus 2. The total number of electrodes connected to both of the first sources and the second sources is equal to the total number of ports of the first sources, and to the total number of ports of the second sources minus 1. The total number of electrodes not connected to the first sources is equal to the total number of ports of the first sources minus 2 and to the total number of electrodes connected to the monitors minus 2. The total number of electrodes not connected to the second sources is equal to the total number of electrodes connected to the monitors minus 3.

Figure 27:
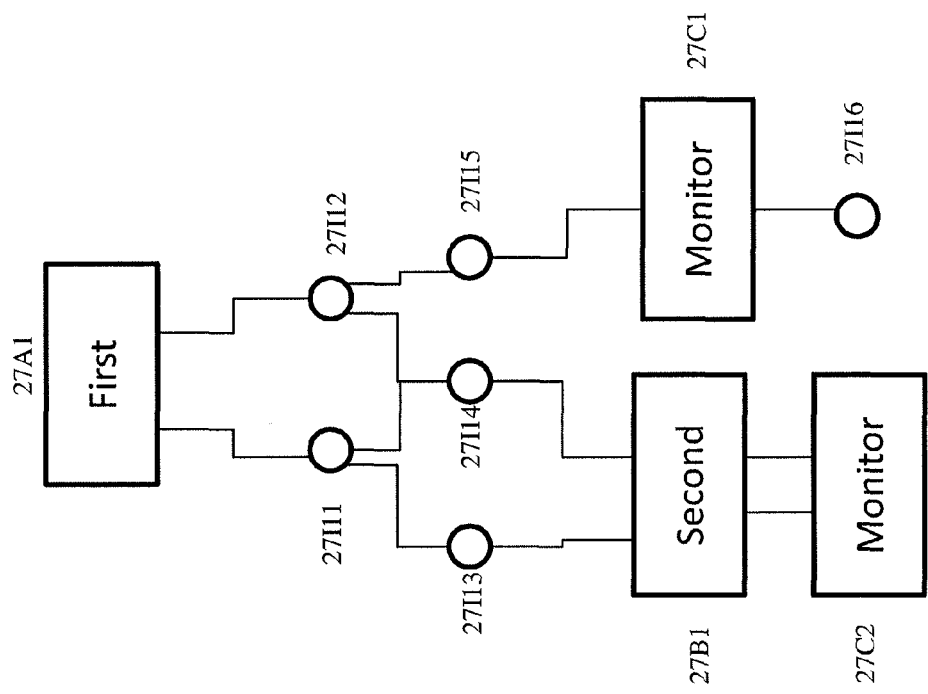

FIG. 27: 27A1 is connected to 27I11 and 27I12. One port of 27I11 and 27I12 are connected to common point 27I14. The other port of 27I11 and 27I12 are connected to 27I13 and 27I15 respectively. 27I13 and 27I14 are connected to 27B1; which is connected to 27C2. 27I15 and 27I16 are connected to 27C1. 27I16 is not connected to 27A1. Generally, the total number of ports of the first source is equal to the total number of ports of the second source and equal to the total number of electrodes minus 4. The total number of electrodes connected to the first source is equal to the number of ports of the first source plus 3 and to the total number of ports of the second source plus 3. The total number of electrodes not connected to both of the first source and the second source is equal to the total number of electrodes connected to the monitor minus 1.

Figure 28:
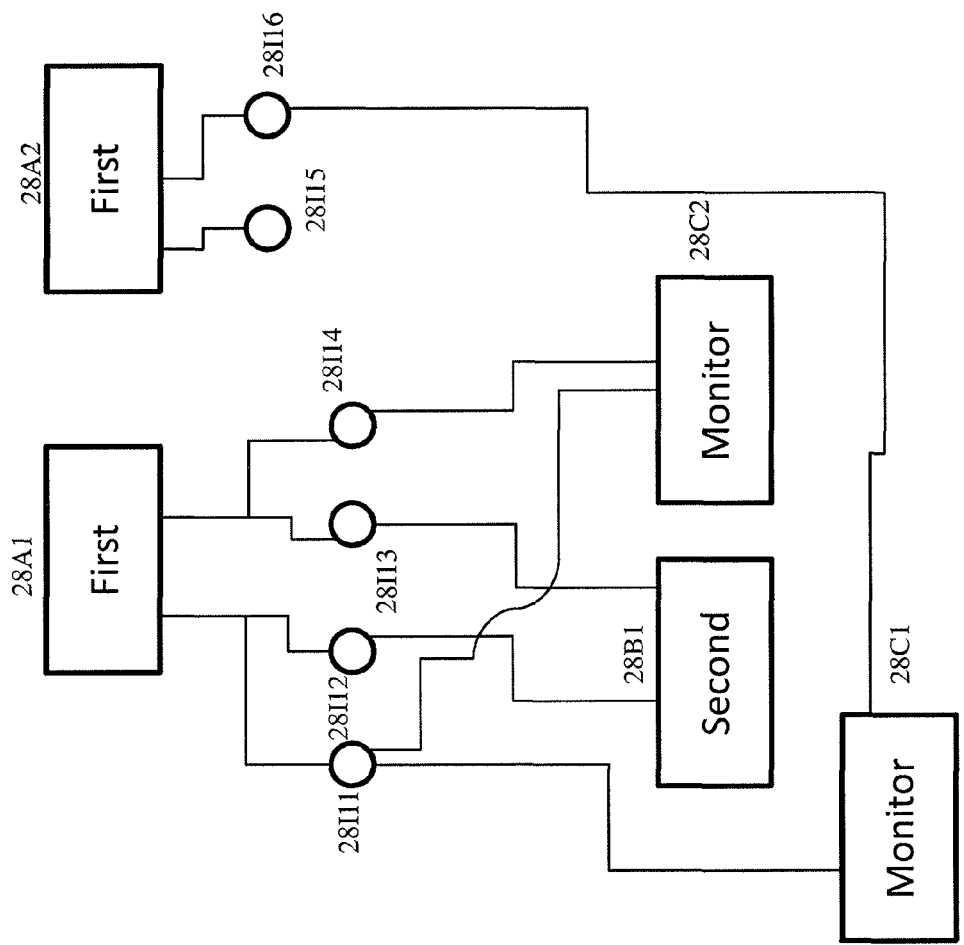

FIG. 28: One port of 28A1 is divided into 28I11, 28I12 whereas the other port of 28A1 is also divided into 28I13, 28I14. 28A2 is connected to 28I15 and 28I16 28I11 and 28I14 are connected to 28C2. 28I12 and 28I13 are connected to 28B1. 28I11 and 28I15 are connected to 28C1. Generally, the total number of ports of the first sources is equal to the total number of ports of the second source plus 2 and equal to the total number of electrodes minus 2. The total number of electrodes connected to both of the first sources and the second source is equal to the number of ports of the first sources minus 2, and to the total number of ports of the second source. The total number of electrodes not connected to the first sources is equal to the number of ports of the first sources minus 4 and total number of electrodes connected to the monitors minus 2. The total number of electrodes not connected to the second source is equal to the total number of electrodes connected to the first sources minus 2.

Figure 29:
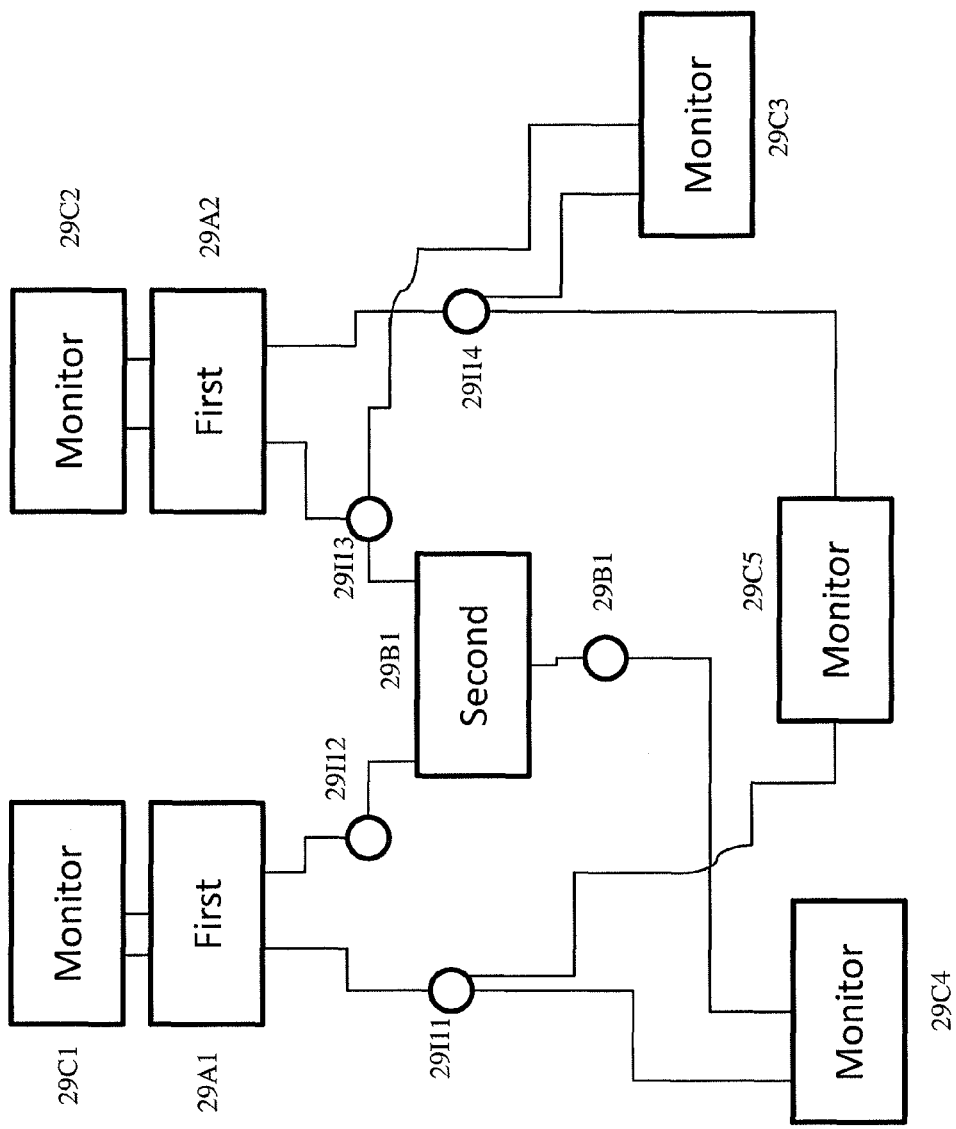

FIG. 29: 29A1 and 29A2 are connected to 29C1 and 29C2 respectively. 29A1 is further connected to 29I11 and 29I12. Similarly 29A2 is connected to 29I13 and 29I14. 29I12 and 29I13 are connected to 29B1. 29B land 29I11 are further connected to 29C4. 29I11 and 29I14 are connected to 29C5. 29I13 and 29I14 are connected to 29C3. Generally, the total number of ports of the first sources is equal to the total number of ports of the second source plus land equal to the total number of electrodes minus 1. The total number of electrodes connected to both of the first sources and the second source is equal to the total number of ports of the first sources minus 2 and to the total number of ports of the second source minus 1. The total number of electrodes not connected to the first sources is equal to the total number of ports of the first sources minus 4 and to the number of electrodes connected to the monitors minus 4. The total number of electrodes not connected to the second source is equal to the total number of electrodes connected to the monitors minus 3.

Figure 30:
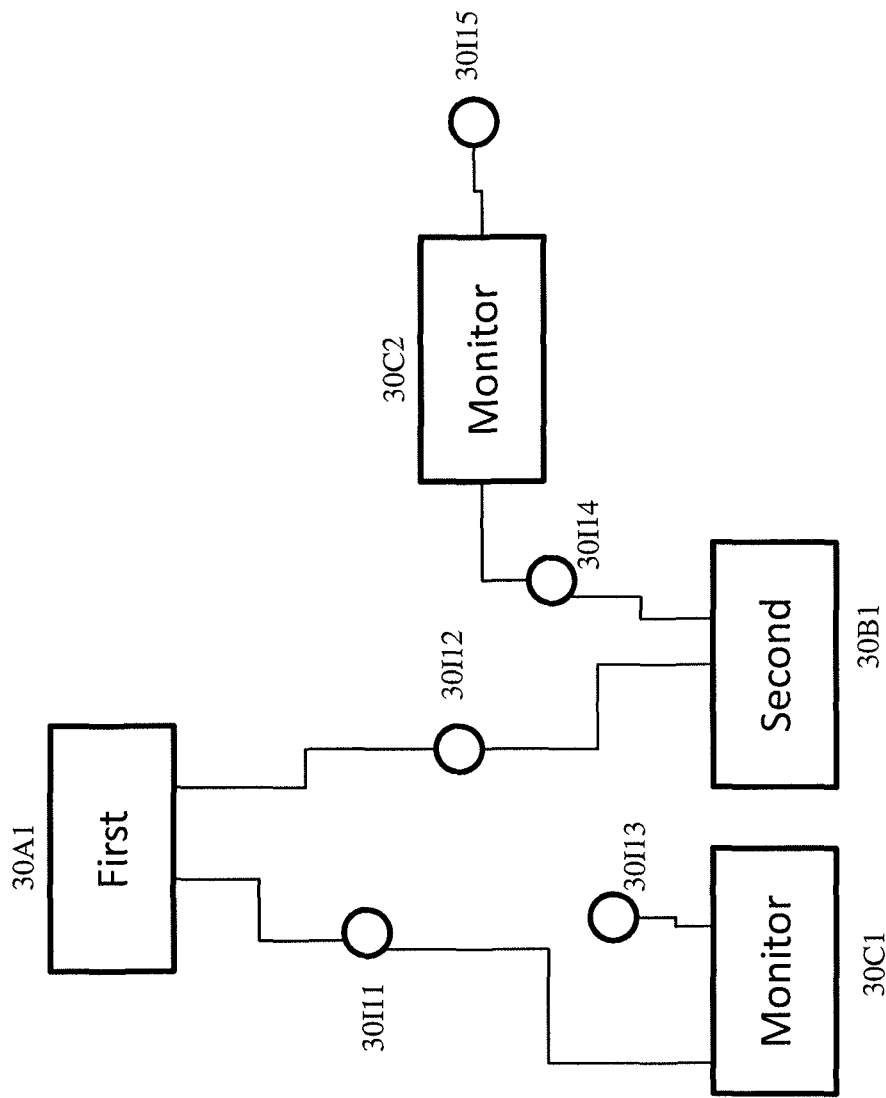

FIG. 30: 30A1 is connected to 30I11 and 30I12. 30I11 and 30I13 are connected to 30C1. 30I13 is not connected to 30A1. 30I12 and 30I14 are connected to 30B1. 30I14 is not to 30A1 either. 30I14 and 30I15 are also connected to 30C2. More generally, the total number of ports of the first source is equal to the total number of ports of the second source and equal to the total number of electrodes minus 3. The total number of electrodes connected to both of the first source and the second source is equal to the total number of ports of the first source minus 1 and to the total number of ports of the second source minus 1. The total number of electrodes not connected to the first source or to the second source is equal to the total number ports of first source plus 1 and to the total number of electrodes connected to the monitors minus 1.

Figure 31:
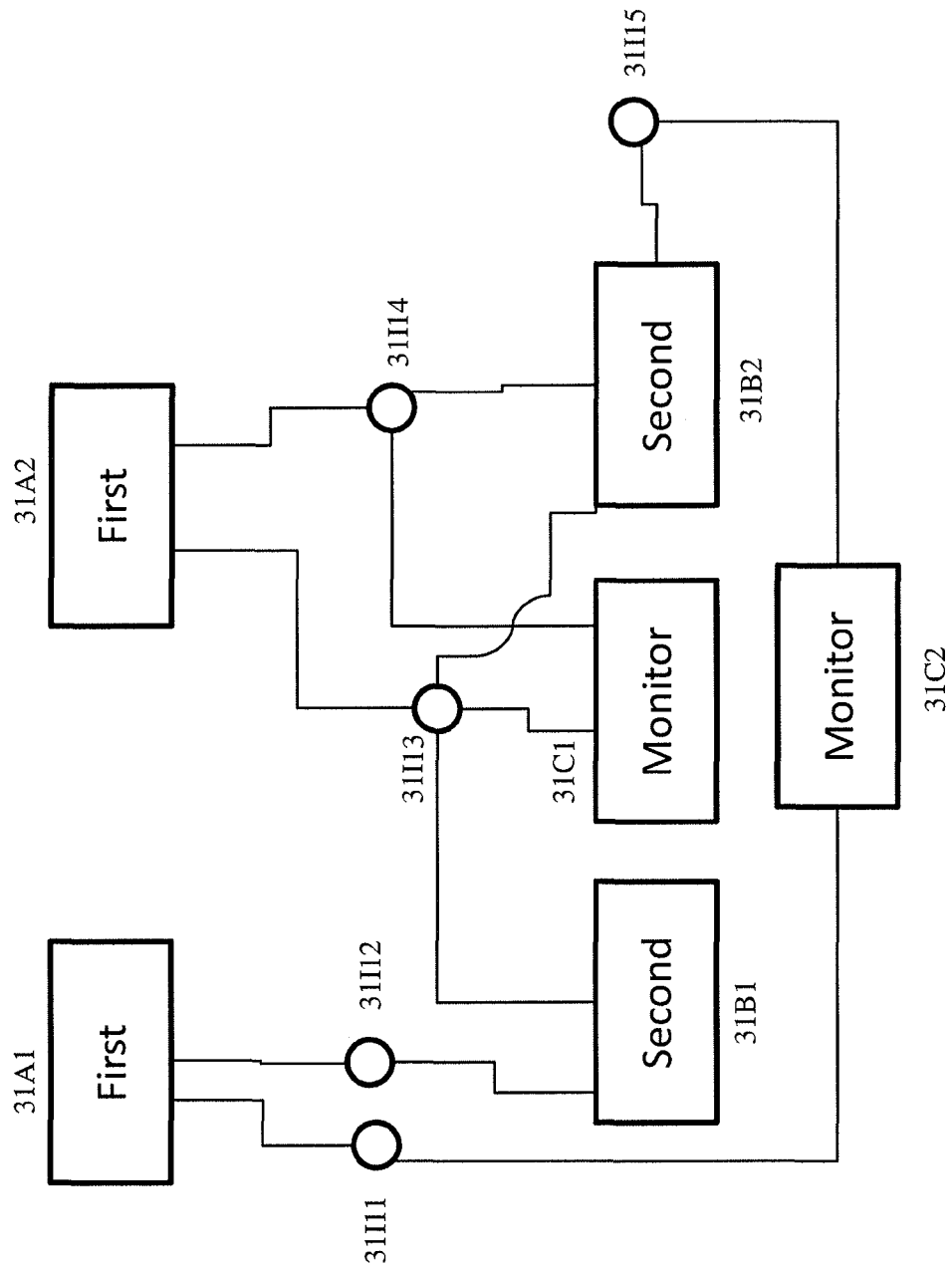

FIG. 31: 31A1 is connected to 31I11 and 31I12. 31A2 is connected to 31I13 and 31I14. 31I12 and 31I13 are further connected to 31B1. 31I13 is further connected to 31C1 and 31B2. 31I14 is connected to 31C1 and 31B2 too. 31I11 and 31I15 are connected to 31C2. 31I15 is neither connected to 31A1 nor to 31A2. Generally, the total number of ports of the first sources is equal to the total number of ports of the second sources and equal to the total number of electrodes minus 1. The total number of electrodes connected to both of the first sources and the second sources is equal to the total number of ports of the first sources minus land to the total number of ports of the second sources minus 1. The total number of electrodes not connected to the first sources or the second sources is equal to the total number of ports of the first sources minus 3, and to the number of ports of one of the second sources minus 1, and the total number of electrodes connected to the monitors minus 3.

Figure 32:
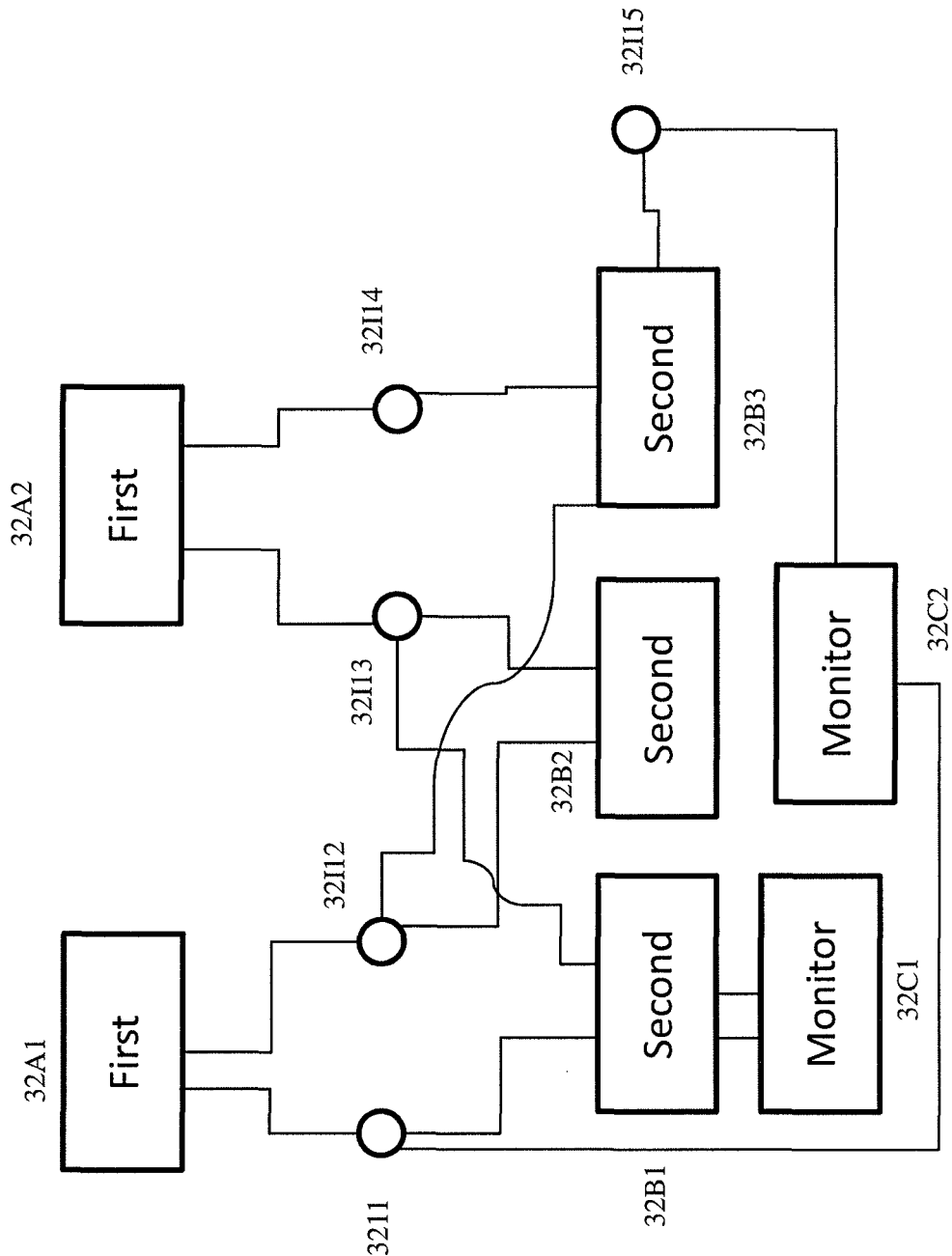

FIG. 32: 32A1 is connected to 32I11, 32I12 whereas 32A2 is connected to 32I13 and 32I14. 32I11 and 32I13 are connected to 32B1; which is connected to 32C1. 32I12 and 32I14 are connected to 32B3. 32I12 and 32I13 are connected to 32B2. 32I11 and 32I15 are further connected to 32C2. 32I15 is not connected to 32A1 or 32A2. In general, the total number of ports of the first sources is equal to the total number of ports of the second sources minus land equal to the total number of electrodes minus 1. The total number of electrodes connected to both of the first sources and the second sources is equal to the total number of ports of the first sources, and to the total number of ports of the second sources minus 1. The total number of electrodes not connected to the first sources is equal to the total number of ports of the first sources minus 3, and to the total number of ports of the second sources minus 4, and to the total number of electrodes connected to the monitors minus 2.

Figure 33:
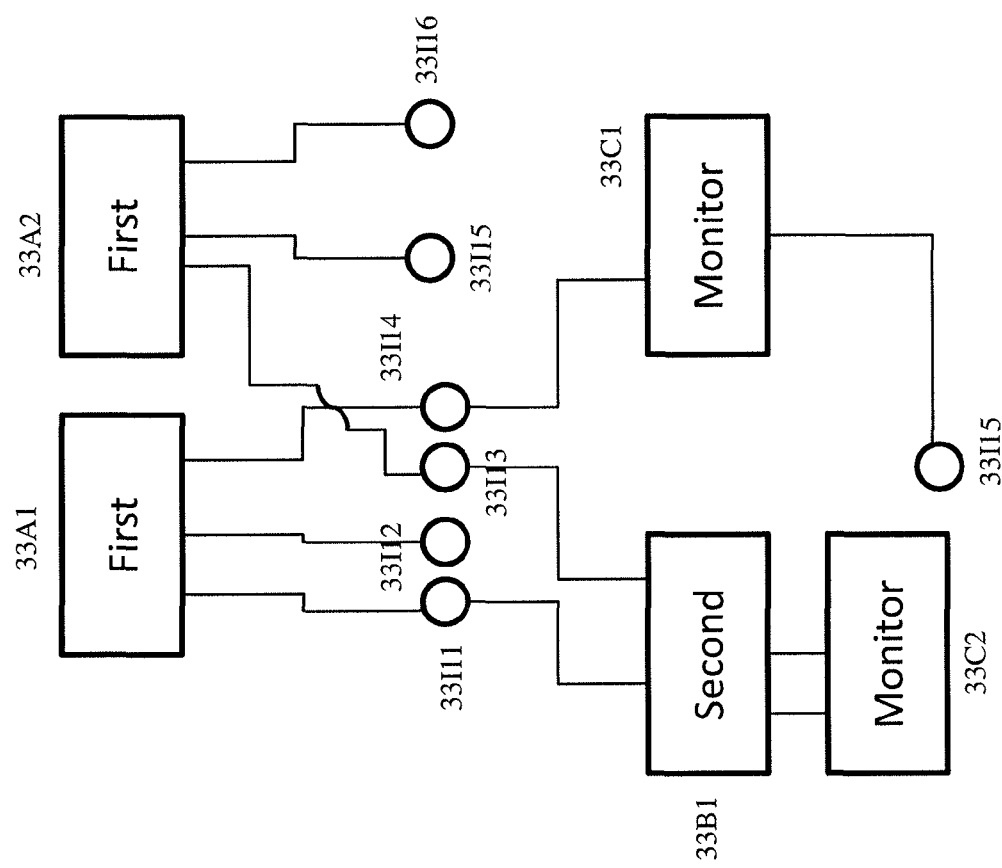

FIG. 33: 33A1 is connected to 33I11, 33I12, and 33I14 whereas 33A2 is connected to 33I13, 33I15 and 33I16. 34I11 and 33I13 are further connected to 33B1; which is connected to 33C2. Likewise, 33I14 and 33I15 are connected to 33C1. 33I15 is neither connected to 33A1 nor to 33A2. More generally, the total number of ports of the first sources is equal to the number of ports of the second source plus 4 and equal to the total number of electrodes minus 1. The total number of electrodes connected to both of the first sources and the second source is equal to the total number of ports of the first sources minus 4 and to the total number of ports of the second source. The total number of electrodes not connected to the first sources is equal to the number of ports of the first sources minus 5.and to the total number of electrodes connected to the monitors minus 1. The total number of electrodes not connected to the second sources is equal to the total electrodes connected to the first sources minus 2.

Figure 34:
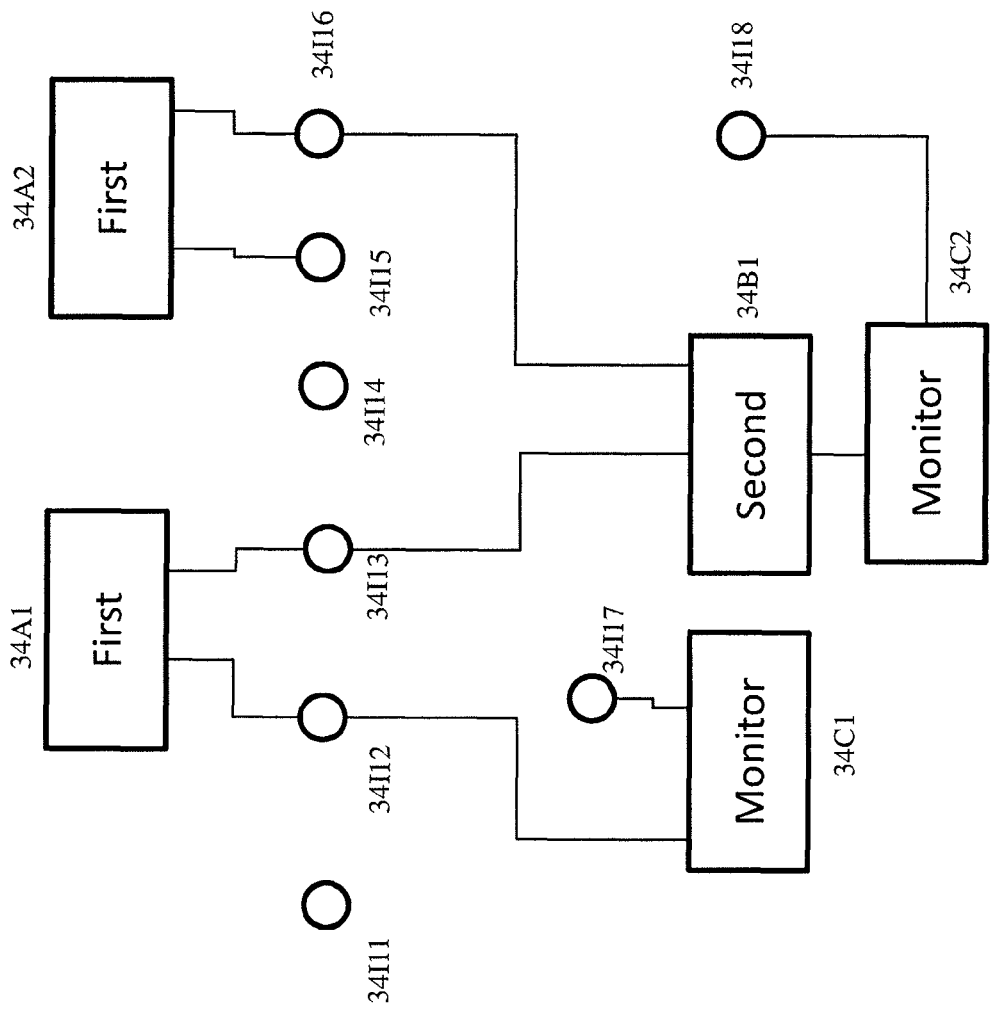

FIG. 34: 34A1 is connected to 34I12 and 34I13 whereas 34A2 is connected to 34I15 and 34I16. 34I11 and 34I13 are no connected to 34A1 or 34A2. 34I12 and 34I17 are connected to 34C1. 34I17 is not connected to 35A1 or 34A2. 34I13 and 34I16 are connected to 34B1. 34B1 and 34I18 are connected to 34C2. 34I18 is neither connected to 34A1 not 34A2. More generally, the total number of ports of the first sources is equal to the total number of ports of the second source plus 2 and equal to the total number of electrodes minus 4. The total number of electrodes connected to both of the first sources and the second source is equal to the total number of ports of the first sources minus 2 and to the total number of ports of the second source. The total number of electrodes not connected to the first sources is equal to the number of ports of the first sources and to the number of electrodes connected to the monitors plus 2. The total number of electrodes not connected to the second source is equal to the total number of electrodes connected to the first sources plus 2.

Figure 40:
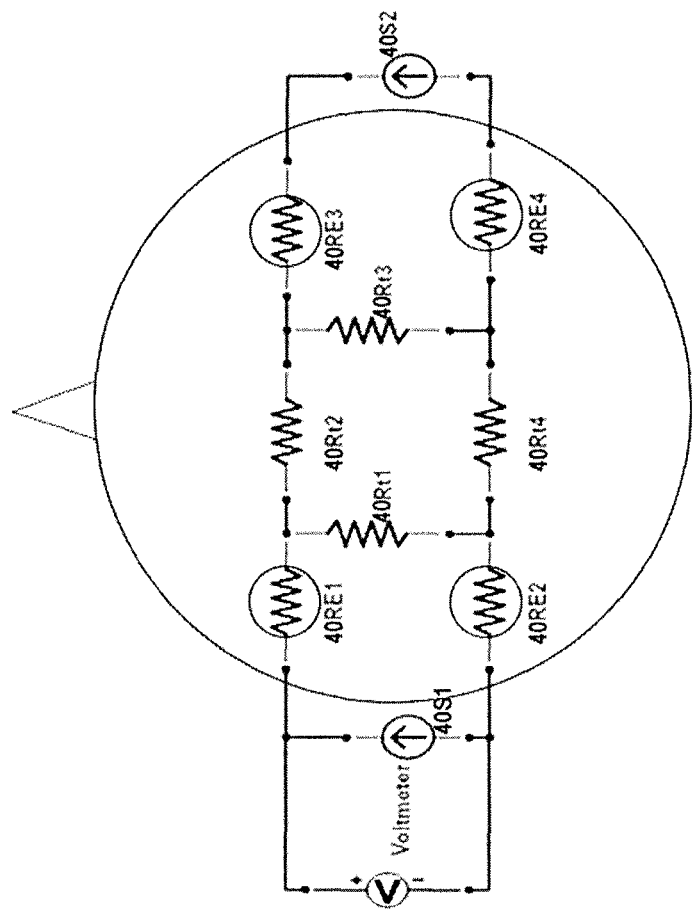
FIG. 40 shows a circuit diagram of head model with two sources and four electrodes, according to some embodiments.

FIG. 40: 40RE1 and 40RE2 connected to 40S1 are placed at some distance from 40RE2 and 40RE4 which are connected to 40S2. The total voltage when both 40S1 and 40S2 are turned on will be a function of 40S1 times the sum of 40RE1, 40RE2, and equivalent tissue impedance and 40S2 times some other equivalent tissue impedance. When the resultant impedance of the tissues in between the electrodes is high, the total voltage will be a product of 40S1 and the sum of 40RE1 and 40RE2. The impedance is preferably less than 10 kΩ. Distance is greater than 2 cm, and preferably greater than 10 cm.

Figure 41:
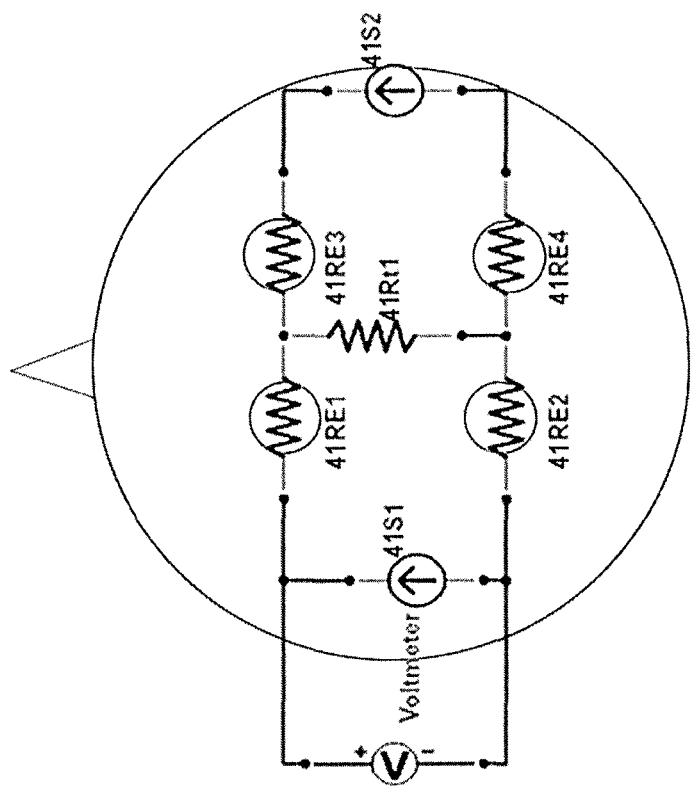
FIG. 41 shows a circuit diagram of head model with two sources and four electrodes placed proximal to each other, according to some embodiments.

FIG. 41: 41RE1 and 41RE2 connected to 41S1 are proximal to 41RE2 and 41RE3 which are connected to 41S2. From the first case, the proximal assembly of 41RE1, 41RE2, 41RE3 and 41RE4 will eliminate 41Rt2 and 41Rt4, and 41Rt3 will go to infinity, resulting in only 41Rt1 impedance among them. The total voltage when both 41S1 and 41S2 are turned on will be a product of 41S1 and the sum of 41RE1, 41RE2, and 41Rt1 & a product of 41S2 and 41Rt1. Distance is less than 10 cm, and preferably less than 5 cm.

Figure 42:
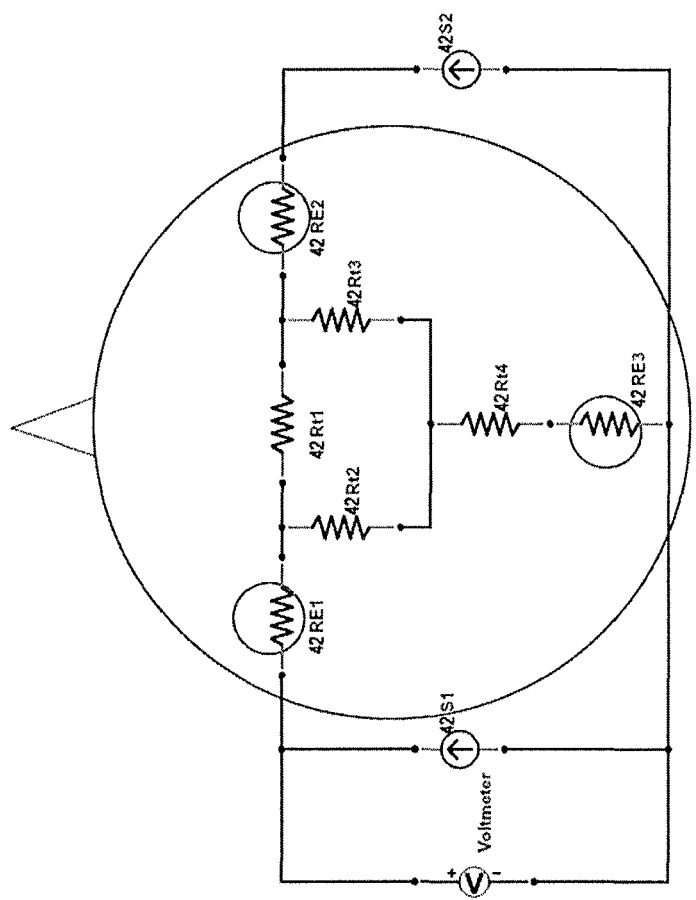
FIG. 42 shows a circuit diagram of head model with two sources connected to two independent electrodes and a shared electrode, according to some embodiments.

FIG. 42: 42RE1 is connected to 42S1 and 42RE2 is connected to 42S2 along with a common electrode 42RE3 which is connected to both 42S1 and 42S2. When both 42S1 and 42S2 are turned on, the total voltage will be a product of 42S1 and the sum of resultant tissue impedance, 42RE1, and 42RE3 & a product of 42S2 and the sum of another resultant impedance of the tissue, and 42RE3. When the resultant tissue impedance will go to infinity, the total voltage will be a product of 42S1 and the sum of 42RE1, 42RE3, and 42Rt4 & a product of 42S2 and the sum of 42RE3 and 42Rt4 times 42S2.

Figure 43:
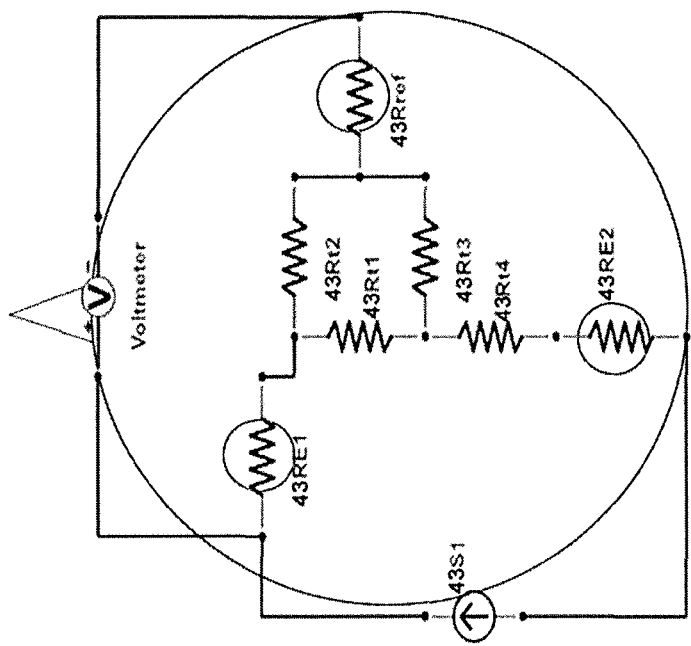
FIG. 43 shows a circuit diagram of head model with one source connected to two electrodes and have an additional sentinel electrode, according to some embodiments.

FIG. 43: 43RE1 and 43RE2 are connected to 43S1 and a sentinel electrode 43Rref is placed at some distance in the horizontal centerline between 43RE1 and 43RE2. The total voltage measured across 43RE1 and 43Rref will be a product 43S1 and the sum of 43RE1 and the resultant tissue impedance in between. High tissue impedance will result in the total voltage that depends upon the product of 43S1 and 43RE1.

Figure 44:
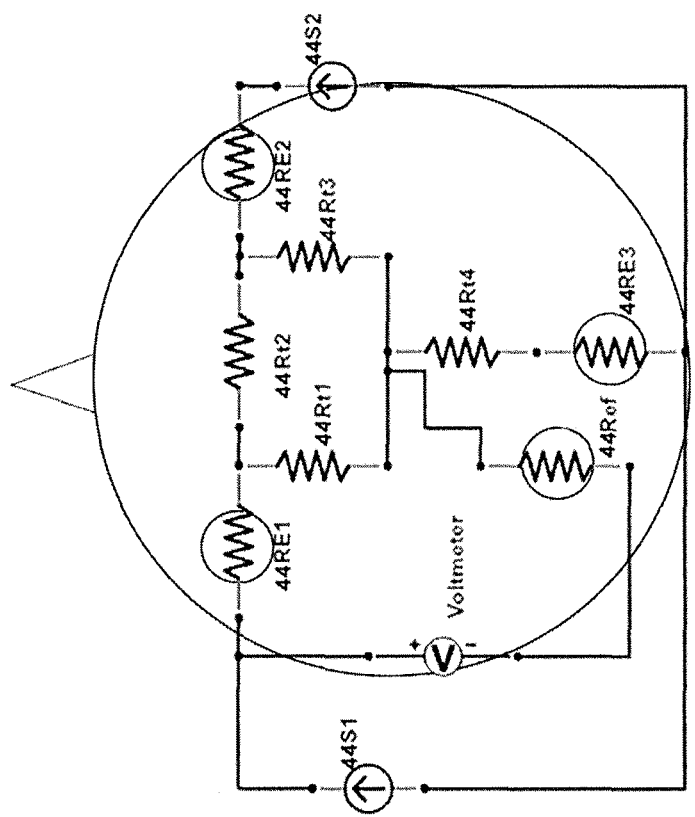
FIG. 44 shows a circuit diagram of head model with two sources connected to two independent electrodes and one shared electrode and have an additional sentinel electrode, according to some embodiments.

FIG. 44: 44RE1 is connected to 44S1, 44RE2 is connected to 44S2, and a shared electrode 44RE3 is connected to both 44S1 and 44S2. In addition to that, a sentinel electrode 44Rref is placed parallel to 44RE3 at some distance. The total voltage across 44RE1 and 44Rref will be a product of 44S1 and the sum of resultant tissue impedance, and 44RE1 & a product of 44S2 and some other tissue impedance. When the resultant tissue impedance is high, the total voltage will be the product of 44S1 and 44RE1.

Triangulation enhances fidelity when at least of first electrical energy source is activated concurrently with at least one second electrical energy source and when the electrodes connected to the first electrical energy source and the electrodes connected to the second electrical energy source are on a distributed impedance load. The electrodes may be shared or independent. The impedance load may include capacitive and non-linear elements, moreover that are time dependent. Triangulation is provided at a time of interest and can be repeated over time such that the processing of tissue and electrode properties is enhanced. Triangulation further leverage the known position of the electrodes, for example if the electrode are positioned according to the 10/20 or 10/10 system and in preferred embodiment the electrodes connected the first electrical energy source and the second electrical energy source are positioned consistent with 4-electrode technique for impedance.

The resulting current flow through the load is a distributed summation of the current flow from each of the first electrical energy sources and each of the second electrical energy sources at governed by the load (e.g. head) properties and the positions of the electrodes as defined above. The voltage generated on the load, and specifically along the surface of the load, will therefore be determined by the net source configuration including the source waveform components (e.g. frequency spectrum) and the aggregate frequency specific tissue properties of the relevant tissues. The use of distinct waveform in at least one of the first electrical energy source and at last one of the second electrical energy source thus restricts the possible voltages (including voltage on the scalp) based on the electrode position, connection of the source to the electrode, and tissue.

For example the use of a DC signal in the primary electrical energy source and a 10 Hz signal the second electrical energy source. In a preferred embodiment, the at least one of the secondary electrical energy sources generated a Gaussian noise which is monitored by a sense resistor as explained below. The voltage across the sense resistor is further provided to the controller. The current provided by the primary and secondary systems can be provided in series or in parallel. The voltage generated, detected by the monitors as described in some embodiments, can be then be processed by the controller to predict properties of the electrode and tissue not possible with approaches not using all these elements. The controller may them inform stimulation montage (for example by changing the stimulation intensity or electrode used). If the load specific cannot be constrained by the initial measurements, then the controller may provide additional frequencies and/or activate addition electrodes via the second electrical energy source. The detailed examples below provide further aspects of computational methods that be integrated with triangulation. The use of a sentinel electrode as described or calculation of the voltage at least one electrode guarantees restriction of the solution.

Electrodes may be optimized and distinct with function. Electrodes of the first type are optimized for sensation with typical a contact area of greater than 1 cm2 and metal/gel formulation optimized to reduce sensation and electrochemical reactions. Electrodes of the first type may be replaced or interchanged using a snap connector or similar connector or a magnet connector. Electrodes of the second type may adapt similar techniques as the first type but may be smaller in contact area or volume for escape between 0.5 cm2 and 1 cm2 contact and a gel volume less than 25% of the first electrode gel volume. Differences in electrode size and formulation provides advantages including cost and compactness and electrode density. Sentinel electrodes of the second type, or more generally electrodes connected to a monitor but not a primary or secondary stimulation, may be gel based or dry electrodes (claim 26). When dry electrodes they may have a distinct shape including a disk with increased toughness where the roughness increases the potential contact area by 200% or more. Roughness may be achieved by plating another metal or by shaping the metal or fusing two or more metals. A disk with extended prongs is one embodiment where 8 or more prongs extend more than 0.1 cm from the disk surface. Annular electrodes may also be used for any electrode type to enhance access to the gel and skin including where an opening greater than 0.3 cm2 is available trying a disk electrode.

The electrical source for electrical activation or Neuromodulation, also discussed as the first electrical source, may be a single or multiple voltage or current source. That source would preferably have an output impedance of greater than 1000 ohms and a stray capacitance of less than 1 μF that confers superior integration with other systems disclosed herein. The current source compliance should be greater than 10 V and preferably less than 65V to provide optimized safety compliance and minimize interaction with sensing circuit as shown in the modeling of the resulting scalp voltage artifact. A sense resistor may be incorporated in the output of the sources or on the lead wires shown. For example a sense resistor a small resistance of less than 100 ohm is added in series with one or more lead wires and the voltage across the sense resistor is monitored using an instrumentation amplifier and then converted through an Analog to Digital converter. The information of processed by the controller.

It is understood that each electrical source described here can be fabricated from one or more circuits without deviating from the embodiments of this disclosure using methods known in the art. The source may include both a voltage controlled and current controlled source.

It will be understood that when methods to employ multiple first electrical sources, secondary electrical sources, or multiple monitors are disclosed (elements) they these can be implemented using distinct circuits for each element or that a single circuit can include multiple elements. Electrical switches and multiplexing circuits may be integrated into the device ether in the lead circuit or embedded within the first or second electrics energy sources or a circuit connected to them. A single electrics source may be used for all primary and or secondary electrical sources while implementing the embodiments disclosed here in.

In one embodiment, one secondary source is used and is connected to each pair of electrodes as shown in the figured through switching such that the secondary sources shown can be replaced by a single source. This confers advantages in signal fidelity by ensuring only one secondary pair of electrodes is concurrently activated. The lead wires in the figures can be replaced with analog or digital switches controlled by a controller to achieve multiple sensing. In a preferred embodiment, during a session of neuromodulation the number of first electrical energy sources is selected (for example 2), and the number of electrodes to be used for stimulation is selected along with the connection from the electrodes to the stimulator (for example 3 electrodes), and the waveform to be applied by the stimulator is selected (for example a DC waveform of 1 mA for 20 minutes). The connection from the first electrical energy sources and the respective connected electrodes is maintained for the stimulation period. Electrodes that will be connected to the secondary electrical energy source are selected (for example 3) and are connected to a single second energy source through a switching device.

During the session, the switching devices connects the electrodes to the single second energy source such that at a given time each desired connection between the secondary electrical energy source and the electrodes is achieved. For example, the second electrical energy source may be connected to each pair wise combination of the three electrodes for 1 second, which continuous cycling between each possible connection for the 20 minutes of stimulation. In this was during stimulation a single second electrical energy source is used to facilitate monitoring and additional benefit such as lack of interference are conferred. The second source may provide the same waveform to each electrode combination (for example 100 Hz, 10 µA to each electrode pair) or may provide a distinct waveform to each pair (for example 100 Hz, 200 Hz, and 300 Hz). The timing of the connections and any changes in waveform may be controlled by the controller and timing information used to analyze information for the monitors. It would be understood that that method can be extended to the other example and system arrangement disclosed here in. It would be understood that monitors are integrated with the above scheme and variation as described elsewhere in this disclosure. The further incorporation of triangulation may be integrated.

Though the controller is not shown in all schematics it would be understood that the controller is connected through a circuit to elements and further may provide control of the function of those elements including the waveform output and lead connection to electrode. The controller may include a microcontroller, a computer, and transmissions methods such as wireless or Bluetooth with an external controller. Digital signal processing as is known on the field would be used by the controller to analyze input from the measuring devices including any monitors or sense resistors and/or performance of the sources such as output voltage. The controller will apply demodulation and necessary or computational methods as described.

Figure 39:
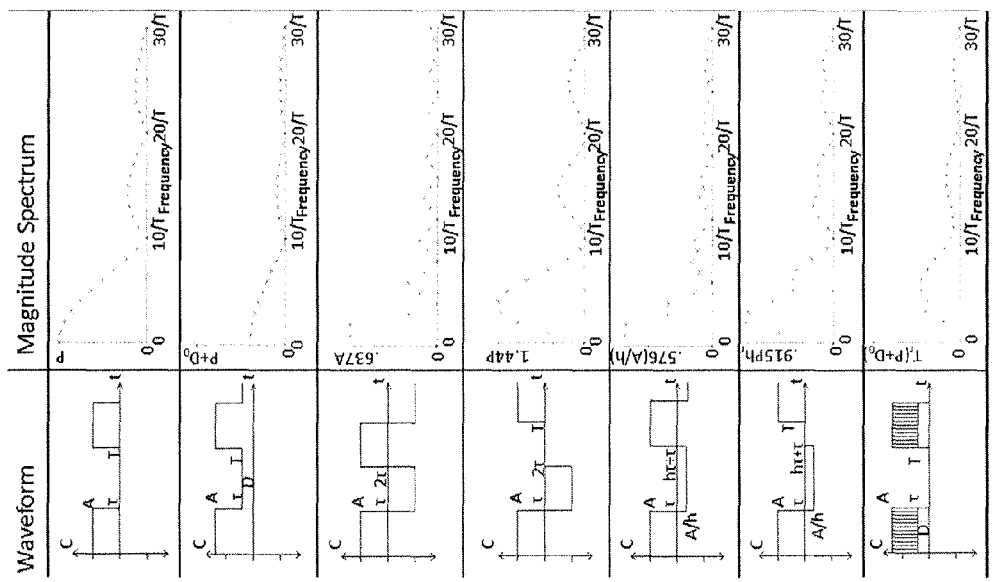
FIG. 39 shows a method to determine the primary and secondary and relevant frequencies of the secondary source or first source, according to some embodiments.

The secondary stimulation source may provide waveforms, such as pulses designed to provide fidelity on the stimulation electrode, stimulation conditions, and/or brain state, while also being designed to avoid interference, crosstalk, and/or mis-triagulation by the controller. The signal detected by the monitor and processed by the controller from any given secondary stimulation electrodes much be processed based on the first stimulation electrodes. The secondary stimulation source may provide a pulse, square wave, or series of pulses. The duty cycle is preferably less than 10% to minimize electrode polarization and facilitate time multiplexing. When at least of the primary electrical energy sources is DC or very low frequency then the pulse with is preferably between 10 µS and 100 ms, and still preferably between 1 mS and 100 ms, with a amplitude preferably between 1 µA and 500 µA and still preferably between 10 µA and 100 µA. These parameters confer benefits to sensation and multiplexing and fidelity of controller processing. The frequency is preferably 0.1 Hz to 100 Hz and still preferably 1 Hz. More generally the primary pulse energy as calculated in FIG. 39 or the secondary pulse energy should be within 1000 Hz and preferably 100 Hz of the primary frequency of the first energy source (which is 0 Hz for the DC case). Thus, in one example, the use of a 5 mS pulse, or 50 µA, applied at 1 Hz by the secondary source, while the primary source uses 1 mA DC would be effective whereas other combinations may produce distortion. The secondary source may also produce a triangle wave or sinusoid. In the case where more than two electrodes and more than two secondary sources are used, the pulse may be multiplexed in time such that the pulse delivered by one secondary source is not delivered at the same time as the same secondary source. This can be extended to multiple electrodes and secondary sources where the timing of activation is controlled or stored on the controller. The use of primary energy source that is DC or very low frequency (such as 1 Hz) confers benefits in separation of the primary energy source signal as detected by one or more monitors and secondary source signal as detected by one more of the monitors when implanted as above. Current controlled stimulation is preferred for both first electrical sources and second electrical sources due to change in electrode impedance.

Figure 35:
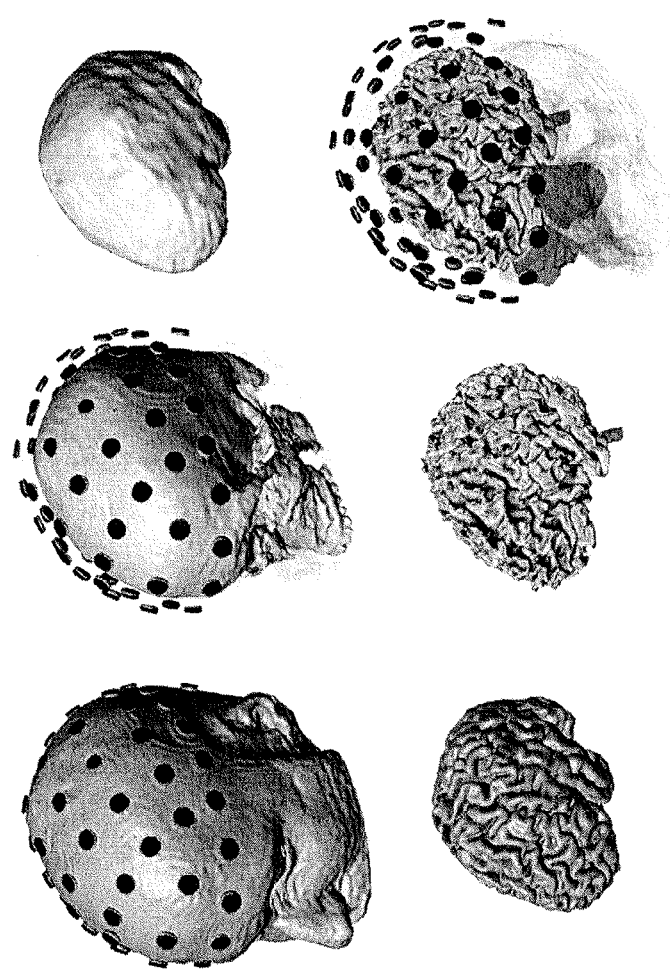
FIG. 35 shows a computational model for current flow with electrodes and tissue, according to some embodiments.

MRI acquisition and segmentation may be implemented in computational methods. MRI of brain can be collected for individually optimized analysis or a general model can be used. For example MRI can be collected using a 3T Philips Achieve a scanner (Philips Medical Systems, Best, Netherlands). Three-dimensional spoiled gradient image (SPGR) was acquired with TE/TR=3 ms/6.6 ms, flip angle=8, acquisition matrix=256×256×190, and voxel size=1×1×1 mm. Automatic segmentation can be performed by FSL's Brain Extraction Tool (BET) (Smith 2002) and FSL's Automated Segmentation Toolbox (FAST) (Zhang et al 2001). The head can be segmented into five compartments: scalp, skull, cerebrospinal fluid (CSF), gray and white matter. Using a combination of segmentation and manual editing tools (Simpleware Ltd, Exeter, United Kingdom). Following the 10-10 international system (conventionally used in EEG), 64 electrodes and gel were automatically positioned on the segmented scalp surface using an in-house custom MATLAB script (Dmochowski et al 2011). All simulated electrodes were ~2 mm thick with a diameter of ~11 mm separated from the scalp by a 1-2 mm thick layer of gel (FIG. 35).

In exemplary tests stimulating electrode configurations were employed though the methods demonstrated may be extended to other electrode configurations. 2 or 6 electrodes were energized as stimulating electrodes according to one of following four electrode configurations tested (see below); the remaining electrodes were not activated. Cz was the ground electrode under all conditions: Several conditions are shown 1) 'Proximal—bipole': Stimulation with two adjacent EEG locations—C2 and Cz., 2) 'Distant—bipole': Stimulation with two distant EEG locations—AF4 and Cz. 3) '4×1 Concentric—Ring': Stimulation with anode electrodes at C3, C4, Fz, Pz enclosing an cathode (ground) electrode at Cz., 4) 'Ring+Bipole': Stimulation combining the distantbipole and the 4×1 concentric-ring configurations with a shared common ground of Cz.

FEM Analysis can be conducted by the controller in conjunction and based on the specific electrode montage. For example, the tissue and the electrode/gel masks were adaptively meshed (Simpleware) and exported into COMSOL Multiphysics (Comsol 3.5a, Burlington, Mass.) for computation of current flow in the head. The classical Laplace equation for volume conduction was solved with a linear iterative system solver of conjugate gradients (relative tolerance=1× 10-6). The following isotropic DC electrical conductivities in (S/m) were assigned: scalp (0.465); skull (0.01); CSF (1.65); gray matter (0.276); white matter (0.126); eye (0.4); muscle (0.334); air (1e-15); electrode (5.8e7); gel (0.3) (Datta et al 2011; Wagner et al 2007). The model comprised >10 million elements with >15 million degrees of freedom.

For the bipolar configurations, current density corresponding to 1 mA total current was applied at the anode electrode. For the 4×1-Ring configuration, each of the anode electrode (s) injected 0.25 mA current resulting in 1 mA total injected anodal current. For the ring+bipole configuration, 1 mA was applied at the AF4 anode electrode and 0.25 mA each was applied at C3, C4, Fz, Pz. Ground boundary condition was applied at the negative electrode (Cz) and all other external surfaces were treated as insulated.

Figure 37:
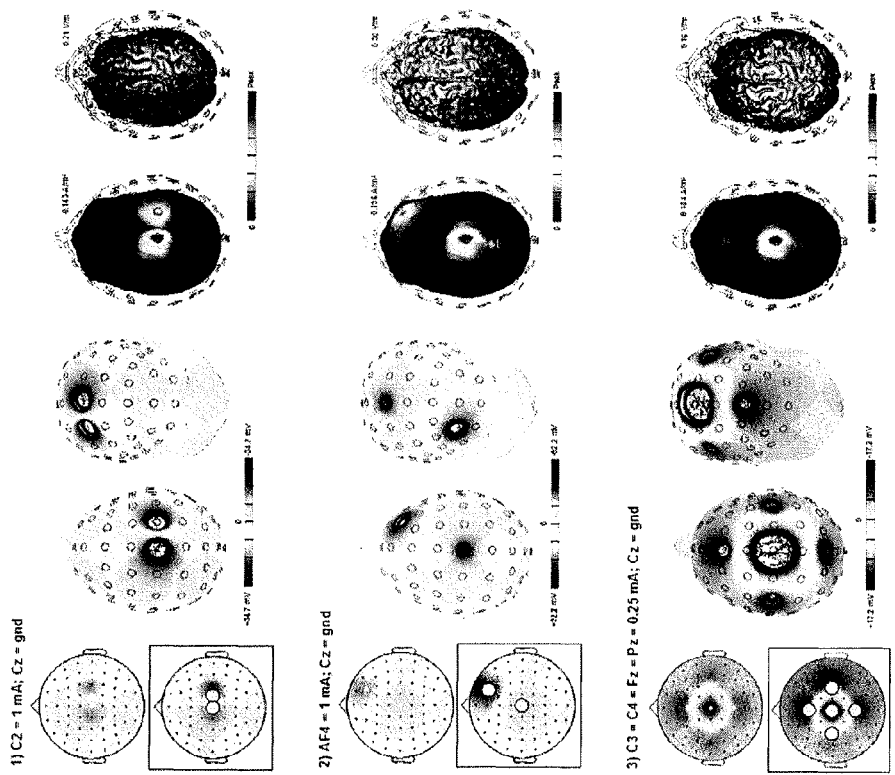
FIG. 37 shows voltages from monitor electrodes during stimulation, according to some embodiments.
Figure 38:
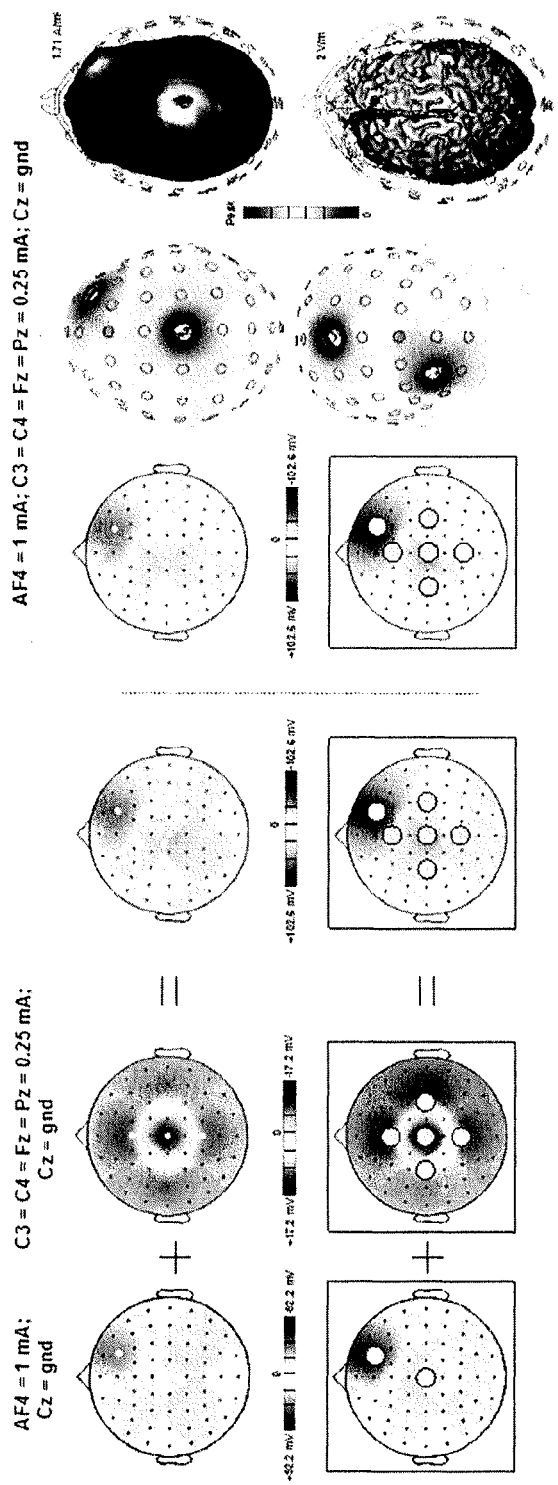
FIG. 38 shows voltages from monitor electrodes during stimulation, according to some embodiments.

Scalp voltage (V), skull current density (A/m2), and cortical electric field (V/m) maps for the different electrode montages were determined (FIGS. 37 and 38). EEG analyses typically use 2-D circular views (topoplot function) providing the ability to visualize all 64 channel locations at once. To enable direct comparison between the experimental and the modeling approaches, induced scalp potentials on each of the 64 electrodes (barring stimulation electrodes) predicted from the FEM models were also displayed via the topoplot function (EEGLAB) (Delorme et al., 2004).

In the example, further transcranial electrical stimulation is implemented with a sentinel electrode monitoring. Low-intensity transcranial electrical stimulation was applied using either an analog isolated current source (Model 2200, A-M Systems, WA) driven by a function generator (Model AFG 320, Tektronix, OR) or stand-alone Soterix 1×1 and 4×1 stimulators. Current was delivered using Ag/AgCl pellet electrodes (A-M Systems, WA) and CCNY-4 gel combination (Minhas et al 2010), where the stimulating electrodes replaced recording electrodes in the head-gear according to the stimulation configuration. The Ag/AgCl pellet stimulation electrodes were specifically chosen so as to match the form-factor of the recording Ag/AgCl electrodes. The electrodes were encased in pin-type electrode holders and mounted into the BioSemi headcaps. The holders were fitted with insets from underneath the cap to ensure a gel contact area corresponding to ~11 mm diameter.

In the first example, linearity of scalp voltages with stimulation intensity and frequency was explored using the proximal-bipolar montage. 0.1 mA, 0.2 mA, 0.4 mA, and 1 mA current intensity (peak) was used and the resulting scalp voltages measured (see below); for each intensity, monophasic square wave (1 Hz) and monophasic (offset) sine wave (1 Hz or 10 Hz) was used. These respond are important to show the ability to use distinct frequency by the second electrical energy source. To minimize skin sensation and avoid irritation while maximizing scalp potential signal-to-noise ratio (S/N), 0.4 mA peak current was used for subsequent experiments. In the second experiment, induced scalp voltage maps were determined for each of the three stimulating electrode configurations. In experiment 3, the spatial linearity of multiple sources was tested by comparing the measured scalp potentials due to the Ring+Bipole configuration to the 4×1 Concentric-Ring and the Distant-bipole configurations independently respectively. A monophasic square wave (1 Hz) or monophasic (offset) sine wave (1 Hz or 10 Hz) waveform was typically used for all mapping measurements in experiments 2 and 3. But, as we validated the linearity of induced scalp potentials with current amplitude (FIG. 36), all results are normalized to per-mA-of-current. Stimulation was applied in repeated exposures of 30 second total duration.

Either implant or surface voltage measurements are provided through measurement. Two example approaches to measure induced scalp potentials; the two technologies yielded identical results and may be extended to the broader montages described here. In one case, scalp potentials were measured sequentially between pairs of electrodes (maintaining a single arbitrary reference) using a custom-made instrumentation amplifier and band-pass filter, with potentials recorded on an oscilloscope. In the second case, scalp potentials were simultaneously measured from all scalp electrodes using the BioSemi EEG (Active Two system, Amsterdam, Netherlands) using packaged A/D and software analysis. In both cases, scalp potentials were measured using electrodes at multiple locations on the scalp following the 10-10 system—omitting the locations occupied by the stimulating electrodes (though the potential applied to the stimulating electrodes could be measured as the output of the current source, we suspected that because of the electrode interface voltage, this potential did not reflect the voltage at the scalp under the stimulation electrodes). The scalp potential distributions are displayed using EEGLAB's topoplot function (see boxed images in FIGS. 37 and 38). Sentinel electrodes detected scalp potentials induced during transcranial electrical stimulation.

Figure 36:
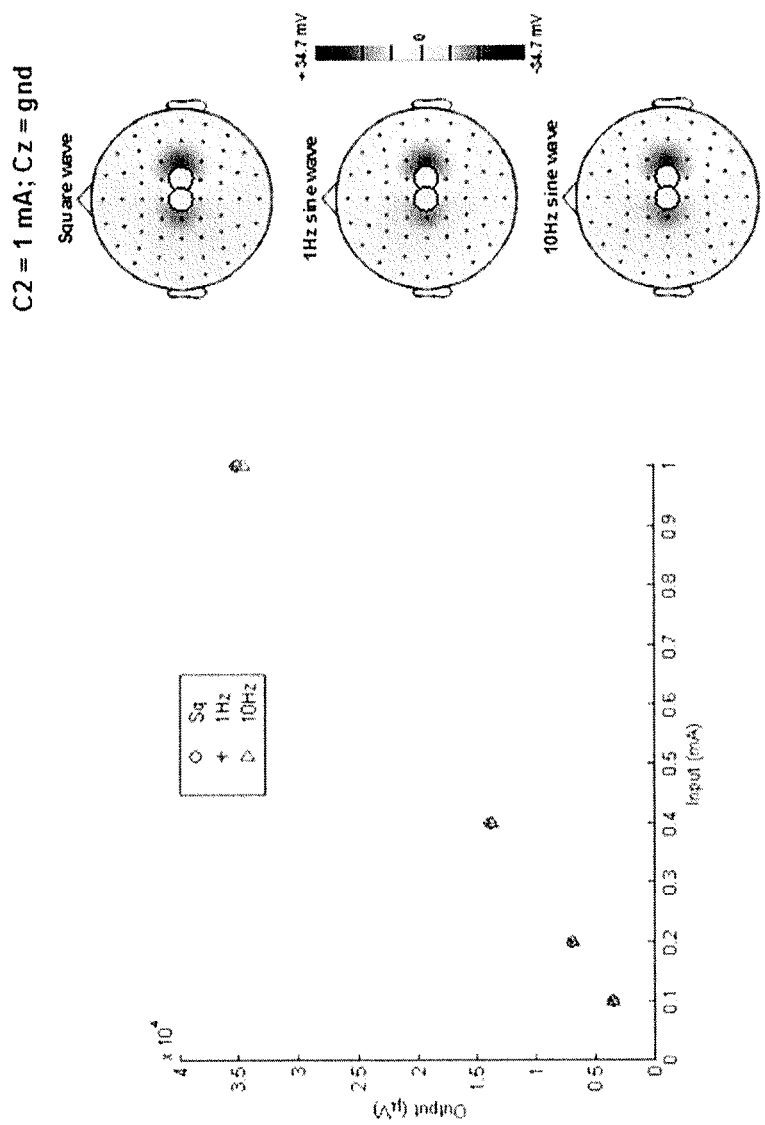
FIG. 36 shows voltages from monitor electrodes during stimulation, according to some embodiments.

Linearity of scalp voltages with stimulation current amplitude and waveform supports analysis based on linear methods implementation for embodiments of the present disclosure. For relatively low frequency and amplitude, we show that scalp voltage amplitude, and by implication tissue current flow, is a linear function of stimulation amplitude. Specifically, the measured peak scalp voltage increases linearly with the applied current (0.1 to 1 mA) between two scalp stimulating electrodes (C2 and Cz); moreover in a frequency independent manner across low-frequencies (square 1 Hz and sine 1 to 10 Hz; FIG. 36) and for frequencies up to 1000 Hz. Similarly, the profile of spatial maps is unchanged across low frequencies. This linearity allows us to normalize spatial maps to per-mA of applied current as well as supports generalizing our results to any stimulation intensity and waveform (e.g. AC, DC) within the linear range. Systems implementing triangulation or more generally providing for monitoring of electrode or tissue impedance during electrical stimulation with one or more first electrical sources thus preferably apply waveforms from secondary electrical sources over frequency ranges and intensity that maintain this unexpected linearity. Specifically low intensity stimulation below 1 mA, and for the secondary sources still below 50 μA for advantages in sensation. Specifically for frequency below 1000 Hz analysis can be made by the controlled across frequencies and using the computational methods described.

Spatial maps of scalp voltages during transcranial electrical stimulation and predicted underlying current distribution such that the controller may be used to guide stimulation. In the example it is shown that measured the scalp voltages induced during transcranial electrical stimulation using four electrode montages. Results from the experimental measurements were compared to predictions of a high-resolution FEM model—which was individualized to the same subject. Each electrode montage resulted in a distinct surface potential map that was precisely predicted by the subject-specific FEM model (FIGS. 37 and 38). For the proximal-bipole stimulation montage, 1 mA injected current led to 34.7 mV peak measured scalp potential. While the FEM simulation predicted a peak value of 31.1 mV. The distant-bipole montage resulted in 92.2 mV peak measured and 77.9 mV peak FEM predicted scalp potential. The 4×1 montage led to 17.2 mV peak measured and 15.1 mV peak model predicted scalp voltage. For each electrode montage, the FEM model also predicts the resulting current flow in deeper tissue including the skull current density and the cortical electric fields (FIG. 37).

Spatial linearity of scalp voltages with multiple stimulation sources can be shown and used by the microcontroller. It is shown that when multiple current stimulators are used, the resulting brain electric fields reflect the independent contribution from each source. This is implemented at the level of the scalp (FIG. 38). Specifically with a 6 electrode configuration that combines the 4×1 configuration and the distant bipolar configuration (with Cz location shared) results in scalp voltages equal to the sum of scalp voltages generated independently by the 4×1 and distant-bipolar configurations. The combined 6-electrode experimental spatial map is also matched by FEM predictions. The peak measured and predicted scalp potentials are 102.6 mV and 85.8 mV respectively.

Linearity in low intensity and frequency transcranial electrical stimulation can be shown and used by the microcontroller. For relatively low-intensity and frequency, linearity in transcranial electrical stimulation indicates that: 1) As the applied current intensity increases, the electric field in all regions scales directly with the current amplitude; 2) The induced electric field tracks the waveform of the applied current, independent over the low frequency range tested; as used, for example, in tACS (Antal et al 2008; Kanai et al 2008) and slow oscillation stimulation (Marshall et al 2006). 3) When multiple current sources are used, the resulting electric fields are a summation of the electric fields induced independently by each current source. This linearity may be leveraged in algorithms on out controller.

Scalp and deeper tissue current flow during transcranial electrical Stimulation can be employed by the controller. For montages, including distant-bipolar, there is current distribution across the entire scalp region between and around electrodes (reflected in a broad scalp voltage distribution). The current density at the skull is however highly localized directly under the stimulation electrodes when optimized. This can be leveraged in designed system as though significant current is shunted tangentially across the scalp, the currents that cross radially through the skull are restricted to under the stimulation electrodes (essentially current that is shunted across the scalp has little driving force to cross the skull). Despite focal current entry across the skull, however, the resulting electric fields across the gray matter are still distributed across the cortical entire region between electrodes. Current entering the brain passes through the entire intermediate brain on the way to the cathode (ground) electrode(s) and the presence of a highly conductive layer of CSF further promotes this broad distribution. Though other have suggested skull is a "low-pass spatial filter" during transcranial electrical flow, diffusing current and severely limiting stimulation focality, the approach here overcomes this perceived limitation. This approach shown here, the system is design such that the high resistivity of the skull leads to predominantly radial (specifically undiffused) current flow.

In a further embodiment the controller implements monitoring of scalp voltage during clinical stimulation and relation to safety and electrode-impedance tomography. Because scalp voltage reflects the stimulation configuration (electrode montage, current intensity) they provide corroboration that a given clinical dose is being applied correctly. A fault in the stimulation device, a sudden problem with an electrode, or misplaced electrodes, will result in a deviation from an expected scalp voltage map (which is not necessarily evident in electrode resistance or stimulator output voltage); we suggest online monitoring of surface (scalp) voltage (OMSV) may be incorporated as a safety feature in a stimulation device. OMSV can be enhanced by, but does not necessarily require, individualized models.

Brain electrode-impedance tomography (EIT) involves application of weak transcranial electrical and measurement of resulting scalp voltage changes for the purpose of imaging brain impedance or brain activity (Abascal et al 2008; Gilad & Holder 2009; Oh et al 2011; Tidswell et al 2001). For EIT typically no a priori individualized information is used (e.g. MRI scans) and indeed the rationale for EIT is predicated on accurately determining (resolving) individual anatomical or functional differences. Other EIT approaches use anatomical data obtained from independent imaging (e.g. MRI). In contrast to EIT, OMSV returns only a binary decision of "correct" or "incorrect" stimulation electrode configuration (placements and faults). OMSV can still leverage the sophistication of analysis tools developed for EIT, especially in the absence of MRI based subject-specific modeling. Recent work in EIT includes: 1) exploration of commercially available FE tools to build accurate meshes with the goal of improving image reconstruction (Bayford et al 2001); 2) incorporation of tissue anisotropy (Abascal et al 2008); 3) rapid generation of patient-specific meshes (Vonach et al 2012); 4) innovative stimulation electrode design (Gilad et al 2007) and 5) approaches to inform specification and optimal electrode placement using EIT as well as Magnetic Detection EIT (MD-EIT) (Gilad et al 2009).

In some embodiments, a system for electrical stimulation capable of providing the above may comprise at least one of a first electrical energy source configured to produce a physiologic change, at least one of a second electrical energy source configured to generate an monitoring electrical signal, at least one of a port connected to at least one of first or second electrical energy source, a lead circuit connecting electrodes to the ports of the first and/or ports of the second electrical energy sources, at least two electrodes are connected by the lead circuit to a port of the first electrical energy source, at least two electrodes are connected by the lead circuit to a port of the second electrical energy source, at least one electrode is connected to by the lead circuit to port of the second electrical energy source and a port of the first electrical energy source, at least two ports, where each first electrical energy source and each second electrical energy source is connected to at least two ports, at least one of a an electrical monitor, a controller capable of computational processes including matrix operation, or triangulation, or modeling derived calculation.

Further such a system made add, where the number of electrodes which pass the electrical signal intended for physiologic change and/or which pass the electrical signal intended to monitoring is less than the sum of number of ports connected to a first electrical energy source and the number of ports connected to a second electrical energy source. Further such a system may be designed where the number of electrodes which pass the electrical signal intended for physiologic change and/or which pass the electrical signal intended to monitoring is less than the number of ports connected to a first electrical energy source or the number of ports connected to a second electrical energy source, whichever is greater of the two numbers of ports.

Multiplexing can be implemented in the system by programming of the controller including for space-division multiplexing (SDM), frequency-division multiplexing (FDM), time-division multiplexing (TDM), and code division multiplexing (CDM). In one example the electrodes are activated through alternate polarization each adjacent electrodes, or through phased activation of leads. Space-division multiplexing can be implanted with different point-to-point wires for different electrodes. One example is a switched star network or a mesh network. Examples are multiple-input and multiple output (MIMO), single-input and multiple-output (SIMO) and multiple-input and single output (MISO) multiplexing. A electrode lead with N possible connections makes it possible to communicate with N multiplexed electrodes. The controlled may implement beam-forming rather than multiplexing.

Various implementations of the embodiments disclosed, in particular at least some of the processes discussed, may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Such computer programs (also known as programs, software, software applications or code) include machine instructions for a programmable processor, for example, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor and the like) for displaying information to the user and a keyboard and/or a pointing device (e.g., a mouse or a trackball) by which the user may provide input to the computer. For example, this program can be stored, executed and operated by the dispensing unit, remote control, PC, laptop, smart-phone, media player or personal data assistant ("PDA"). Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Certain embodiments of the subject matter described herein may be implemented in a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet. Communications may be wireless (e.g., cellular, Wi-Fi, Bluetooth), and/or wireline.

The computing system according to some such embodiments described above may include clients and servers. A client and server are generally remote from each other and typically interact through a communication network. The relationship of client and server arises by virtue of computer programs running on the respective computers and having a client-server relationship to each other.

Any and all references to publications or other documents, including but not limited to, patents, patent applications, articles, webpages, books, etc., presented anywhere in the present application, are herein incorporated by reference in their entirety.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to the express embodiments directed toward medical therapy devices. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Correspondingly, some embodiments of the present disclosure may be patentably distinct from one and/or another reference by specifically lacking one or more elements/features. In other words, claims to certain embodiments may contain negative limitation to specifically exclude one or more elements/features resulting in embodiments which are patentably distinct from the prior art which include such features/elements.

REFERENCES

Van Den Eerenbeemd et al. KONINKLIJKE PHILIPS ELECTRONICS N.V. (2011), Wearable device and system for a tamper free electric stimulation of a body, 0087300 A1.

Adams E. Apparatus and method for invasive electrical stimulation of bone fractures (1986), 4602638.

Loeb G E. Alfred E. Mann Institute for Biomedical Engineering at the University of Southern California (2003) Method of apparatus for control of bowel function, 6658297.

http://medical-dictionary.thefteedictionary.com/electroporation

Lovell et al. University of Pittsburgh of The Commonwealth System of Higher Education (2010), Handheld electrical stimulation device, 0191174 A1.

Freeman G A. ZOLL Medical Corporation (2005), Microperfusive electrical stimulation, 0234515 A1.

Steinhaus et al. Telectronics Pacing Systems Inc, (1993). Minute volume rateresponsive pacemaker employing impedance sensing on a unipolar lead, 5201808.

Abascal J F, Arridge S R, Atkinson D, Horesh R, Fabrizi L, et al. 2008. Use of anisotropic modelling in electrical impedance tomography: description of method and preliminary assessment of utility in imaging brain function in the adult human head. Neuroimage 43:258-68.

Antal A, Boros K, Poreisz C, Chaieb L, Terney D, Paulus W. 2008. Comparatively weak after-effects of transcranial alternating current stimulation (tACS) on cortical excitability in humans. Brain Stimul 1:97-105.

Bikson M, Datta A, Rahman A, Scaturro J. 2010. Electrode montages for Tdcs and weak transcranial electrical stimulation: role of "return" electrode's position and size. Clin Neurophysiol 121:1976-8.

Borckardt J J, Bikson M, Frohman H, Reeves S T, Datta A, et al. 2012. A pilot study of the tolerability and effects of high-definition transcranial direct current stimulation (HD-tDCS) on pain perception. J Pain 13:112-20.

Calancie B, Harris W, Broton J G, Alexeeva N, Green B A. 1998. Threshold-level multipulse transcranial electrical stimulation of motor cortex for intraoperative monitoring of spinal motor tracts: description of method and comparison to somatosensory evoked potential monitoring Journal of Neurosurgery 88:457-70.

Dasilva A F, Mendonca M E, Zaghi S, Lopes M, Dossantos M F, et al. 2012. tDCSInduced Analgesia and Electrical Fields in Pain-Related Neural Networks in Chronic Migraine. Headache.

Datta A, Baker J M, Bikson M, Fridriksson J. 2011. Individualized model predicts brain current flow during transcranial direct-current stimulation treatment in responsive stroke patient. Brain Stimul 4:169-74.

Datta A, Bansal V, Diaz J, Patel J, Reato D, Bikson M. 2009. Gyri-precise head model of transcranial direct current stimulation: Improved spatial focality using a ring electrode versus conventional rectangular pad Brain Stimulation 2:201-7.

Datta A, Elwassif M, Battaglia F, Bikson M. 2008. Transcranial electrical stimulation focality using disc and ring electrode configurations:FEM analysis. Journal of neural engineering 5:163-74.

Dmochowski J P, Datta A, Bikson M, Su Y, Parra L C. 2011. Optimized multielectrode stimulation increases focality and intensity at target. J Neural Eng 8:046011.

Dymond A M, Coger R W, Serafetinides E A. 1975. Intracerebral current levels in man during electrosleep therapy. Biol Psychiatry 10:101-4.

Faria P, Hallett M, Miranda P C. 2011. A finite element analysis of the effect of electrode area and inter-electrode distance on the spatial distribution of the current density in tDCS. J Neural Eng 8:066017.

Ferdjallah M, Bostick F X, Jr., Barr R E. 1996. Potential and current density distributions of cranial electrotherapy stimulation (CES) in a four-concentric-spheres model. IEEE Trans Biomed Eng 43:939-43.

Fregni F, Boggio P S, Nitsche M A, Bermpohl F, Antal A, et al. 2005. Anodal transcranial direct current stimulation of prefrontal cortex enhances working memory. Experimental Brain Research 166:23-30.

Gilad O, Holder D S. 2009. Impedance changes recorded with scalp electrodes during visual evoked responses: implications for Electrical Impedance Tomography of fast neural activity. Neuroimage 47:514-22.

Halko M A, Datta A, Plow E B, Scaturro J, Bikson M, Merabet L B. 2011. Neuroplastic changes following rehabilitative training correlate with regional electrical field induced with tDCS. Neuroimage 57:885-91.

Im C H, Park J H, Shim M, Chang W H, Kim Y H. 2012. Evaluation of local electric fields generated by transcranial direct current stimulation with an extracephalic reference electrode based on realistic 3D body modeling. Phys Med Biol 57:2137-50.

Kanai R, Chaieb L, Antal A, Walsh V, Paulus W. 2008. Frequency-dependent electrical stimulation of the visual cortex. Curr Biol 18:1839-43.

Lisanby S H. 2007. Electroconvulsive therapy for depression. N Engl J Med 357:1939-45.

Marshall L, Helgadottir H, Molle M, Born J. 2006. Boosting slow oscillations during sleep potentiates memory. Nature 444:610-3.

Mendonca M E, Santana M B, Baptista A F, Datta A, Bikson M, et al. 2011. Transcranial DC Stimulation in Fibromyalgia: Optimized Cortical Target Supported by High-Resolution Computational Models. Journal of Pain 12:610-7.

Minhas P, Bansal V, Patel J, Ho J S, Diaz J, et al. 2010. Electrodes for high definition transcutaneous DC stimulation for applications in drug delivery and electrotherapy, including tDCS. J Neurosci Methods 190:188-97.

Miranda P C, Lomarev M, Hallett M. 2006. Modeling the current distribution during transcranial direct current stimulation. Clin Neurophysiol 117:1623-9.

Oh T, Gilad O, Ghosh A, Schuettler M, Holder D S. 2011. A novel method for recording neuronal depolarization with recording at 125-825 Hz: implications for imaging fast neural activity in the brain with electrical impedance tomography. Med Biol Eng Comput 49:593-604.

Parazzini M, Fiocchi S, Rossi E, Paglialonga A, Ravazzani P. 2011. Transcranial direct current stimulation: estimation of the electric field and of the current density in an anatomical human head model. IEEE Trans Biomed Eng 58:1773-80.

Rothwell J, Burke D, Hicks R, Stephen J, Woodforth I, Crawford M. 1994. Transcranial electrical stimulation of the motor cortex in man: further evidence for the site of activation. J Physiol 481 (Pt 1):243-50.

Rush S, Driscoll D A. 1968. Current distribution in the brain from surface electrodes. Anesth Analg 47:717-23.

Sadleir R J, Vannorsdall T D, Schretlen D J, Gordon B. 2010. Transcranial direct current stimulation (tDCS) in a realistic head model. Neuroimage 51:1310-8.

Salvador R, Mekonnen A, Ruffini G, Miranda P C. 2010. Modeling the electric field induced in a high resolution head model during transcranial electrical stimulation. Conf Proc IEEE Eng Med Biol Soc 2010:2073-6.

Saypol J M, Roth B J, Cohen L G, Hallett M. 1991. A theoretical comparison of electric and magnetic stimulation of the brain. Ann Biomed Eng 19:317-28.

Schroeder M J, Barr R E. 2001. Quantative analysis of the electroencephalogram during cranial electrotherapy stimulation. Clinical Neurophysiology 112:2075-83 Smith S M. 2002. Fast robust automated brain extraction. Hum Brain Mapp 17:143-55.

Stecker M M. 2005. Transcranial electric stimulation of motor pathways: a theoretical analysis. Comput Biol Med 35:133-55.

Suh H S, Lee W H, Cho Y S, Kim J H, Kim T S. 2010. Reduced spatial focality of electrical field in tDCS with ring electrodes due to tissue anisotropy. Conf Proc IEEE Eng Med Biol Soc 2010:2053-6.

Tidswell T, Gibson A, Bayford R H, Holder D S. 2001. Three-dimensional electrical impedance tomography of human brain activity. Neuroimage 13:283-94.

Wagner T, Fregni F, Fecteau S, Grodzinsky A, Zahn M, Pascual-Leone A. 2007. Transcranial direct current stimulation:a computer-based human model study Neuroimage 35:1113-24.

Windhoff M, Opitz A, Thielscher A. 2011. Electric field calculations in brain stimulation based on finite elements: An optimized processing pipeline for the generation and usage of accurate individual head models. Hum Brain Mapp.

What is claimed is:

1. An electrode based therapeutic treatment system for stimulating tissue to effect a physiological effect comprising:
a plurality of current sources, each current source having a positive output and a negative output and each being configured to provide a first current;
a plurality of stimulating electrodes electrically connected with the plurality of current sources such that at least a pair of the stimulating electrodes share at least one output of at least one of the plurality of current sources, the stimulating electrodes configured to provide electrical energy to tissue of a patient at the first current;
at least one sentinel electrode; and
a first voltage monitor configured to monitor a first voltage across the at least one sentinel electrode and at least one of the plurality of stimulating electrodes.

2. The system of claim 1, wherein the at least one sentinel electrode is not connected to any of the plurality of current sources.

3. The system of claim 1, further comprising a controller configured for at least controlling the output of at least one of the plurality of current sources based upon at least the first voltage.

4. The system of claim 1, further comprising a second voltage monitor for monitoring the voltage across at least a pair of outputs of at least one of the plurality of current sources.

5. The system of claim 1, wherein the current sources are configured to supply at least a DC current.

6. The system of claim 1, wherein an increase in the first voltage between the at least one sentinel electrode and the at least one stimulating electrode corresponds to an increase in voltage of the at least one stimulating electrode.

7. The system of claim 1, wherein
the at least one sentinel electrode comprises a plurality of sentinel electrodes,
each sentinel electrode is paired with a specific stimulating electrode, and
the first monitor is configured to monitor the voltage between each sentinel electrode and a respective stimulating electrode.

8. The system of 1, wherein the at least one stimulating electrode is configured to pass electrical energy from the at least one current source to the tissue to effect physiological change.

9. The system of claim 1, wherein a first current source of the plurality of current sources provides current at a first frequency less than or equal to about 100 Hz.

10. The system of claim 9, wherein a second current source of the plurality of current sources provides current at a second frequency distinct from the first frequency.

11. The system of claim 10, wherein the second frequency is less than or equal to about 10 kHz.

12. The system of claim 1, wherein at least one of the plurality of current sources includes a DC component.

13. The system of claim 1, further comprising a controller having computer instructions operating thereon configured for receiving information from the first voltage monitor and determining voltage across the at least one sentinel electrode and at least one of the plurality of stimulating electrodes based on a computation model of current flow.

14. The system of claim 13, wherein the computational model includes a representation of the tissue and the position of at least one of the stimulating electrode and the sentinel electrode relative to the tissue.

15. The system of claim 13, wherein the computer instructions are further configured to receive anatomical specific information for use by the computation model.

16. The system of claim 15, wherein the anatomical specific information comprises at least MRI.

17. The system of claim 13, wherein the computer instructions are further configured to perform a test phase at the determined voltage.

18. The system of claim 17, wherein only one first current source is activated during the test phase.

19. The system of claim 7, wherein the at least one sentinel electrode comprises either a semi-dry or dry-electrode.

20. The system of claim 1, wherein the plurality of stimulating electrodes comprise two stimulating electrodes and the at least one sentinel electrode comprises a single sentinel electrode.

21. The system of claim 1, wherein current produced by each current source of the plurality of current sources is configured with at least one of a waveform and frequency distinguishable from one another.

22. The system of claim 1, wherein at least two of the current sources are frequency multiplexed.

23. The system of claim 1, wherein at least two of the current sources are time multiplexed.

24. The system of claim 1, wherein each stimulating electrode is connected to each current source.

25. A device for electrical stimulation comprising:
at least two electrodes in contact with the body or tissue,
a circuit connected to the two electrodes,
a monitor, and
a controller having operational thereon computer instructions configured to perform computational processes including at least one of matrix operation, triangulation, and modeling,
wherein
at least one electrical source produces a waveform with at least two components, at least one said components is configured for detection by the monitor and distinguishable by at least one of the computational processes, at least of one of the components of the waveform produces a physiological change at least one of the components is configured to interrogate the status of at least one of the electrodes, and the body or tissue, and the circuit is configured to determine which electrodes receive with waveform components.

26. An electrode based therapeutic treatment system for stimulating tissue to effect a physiological effect comprising:

a plurality of current sources, each current source having a positive output and a negative output and each being configured to provide a first current, wherein;

a plurality of stimulating electrodes configured to be placed adjacent tissue, the stimulating electrodes electrically connected with the plurality of current sources such that at least a pair of the stimulating electrodes share at least one output of at least one of the plurality of current sources, the stimulating electrodes configured to provide electrical energy to tissue of a patient at the first current; and a voltage monitor configured for monitoring the voltage across at least a pair of outputs of at least one of the plurality of current sources, wherein at least one of the plurality of current sources is configured to supply current at a first distinguishable characteristic from the current supplied by at least one other current source.

27. The system of claim 26, wherein the characteristic comprises at least one of a frequency and a phase.

28. The system of claim 26, wherein at least two of the current sources share one electrode.

29. The system of claim 26, wherein the at least one sentinel electrode is not connected to any of the plurality of current sources.

30. The system of claim 26, wherein at least one sentinel electrode is not connected to any current source producing a current intended for therapeutic treatment.

* * * * *